(12) United States Patent
Ben-Neriah et al.

(10) Patent No.: US 9,623,109 B2
(45) Date of Patent: Apr. 18, 2017

(54) METHODS OF KILLING CELLS AND USE OF SAME IN PREVENTION AND TREATMENT OF CANCER

(75) Inventors: Yinon Ben-Neriah, Mevasseret Zion (IL); Ela Elyada, Kibbutz BeErot Yitzchak (IL); Ariel Pribluda, Beer-Sheva (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 585 days.

(21) Appl. No.: 12/994,856

(22) PCT Filed: May 26, 2009

(86) PCT No.: PCT/IL2009/000526
§ 371 (c)(1),
(2), (4) Date: Nov. 28, 2010

(87) PCT Pub. No.: WO2009/144719
PCT Pub. Date: Dec. 3, 2009

(65) Prior Publication Data
US 2011/0076282 A1 Mar. 31, 2011

Related U.S. Application Data

(60) Provisional application No. 61/071,947, filed on May 27, 2008.

(51) Int. Cl.
*A61K 45/06* (2006.01)
(52) U.S. Cl.
CPC .................................. *A61K 45/06* (2013.01)
(58) Field of Classification Search
None
See application file for complete search history.

(56) References Cited

U.S. PATENT DOCUMENTS

2005/0171005 A1  8/2005  Ben-Neriah et al.

FOREIGN PATENT DOCUMENTS

WO  WO 2005/046726  5/2005
WO  WO 2009/144719  12/2009

OTHER PUBLICATIONS

International Preliminary Report on Patentability Dated Dec. 9, 2010 From the International Bureau of WIPO Re. Application No. PCT/IL2009/000526.
International Search Report and the Written Opinion Dated Mar. 23, 2010 From the International Searching Authority Re. Application No. PCT/IL2009/000526.
Brockschmidt et al. "Anti-Apoptotic and Growth-Stimulatory Functions of CK1 Delta and Epsilon in Ductal Adenocarcinoma of the Pancreas are Inhibited by IC261 In Vitro and In Vivo", GUT, XP009130010, 57(6): 799-806, Jan. 18, 2008. Abstract.
Brockschmidt et al. "The CK1δ/ε Specific Inhibitor IC261 Abolishes the Growth of Pancreatic Tumor Cells and Sensitizes Pancreatic Tumor Cells Against CD95-Mediated Apoptosis", Chirurgisches Forum 2006 für Experimentelle und Klinische Forschung, 123. Kongress der Deutschen Gesellschaft für Chirurgic, Berlin, May 2-May 5, 2006, XP009130022, p. 145-146, Jan. 1, 2006.
Chen et al. "Regulation of P53-MDMX Interaction by Casein Kinase 1 Alpha", Molecular and Cellular Biology, 25(15): 6509-6520, Aug. 2005.
Stöter et al. "Inhibition of Casein Kinase I Delta Alters Mitotic Spindle Formation and Induces Apoptosis in Trophoblast Cells", Oncogene, XP002571143, 24(54): 7964-7975, Dec. 2005. Abstract, p. 7973, col. 1, Last §.

*Primary Examiner* — Jennifer McDonald

(57) ABSTRACT

A method of killing a cell having a mutation in an Adenomatous polyposis coli (APC) gene is disclosed. The method comprises contacting the cell with an inhibitor of Casein kinase I (CKI), the CKI being selected from the group consisting of CKI-alpha and CKI-delta and CKI-epsilon, thereby killing the cell. The method may be used for treating cancers. Pharmaceutical compositions for treatment of cancers are also disclosed.

11 Claims, 35 Drawing Sheets

(33 of 35 Drawing Sheet(s) Filed in Color)

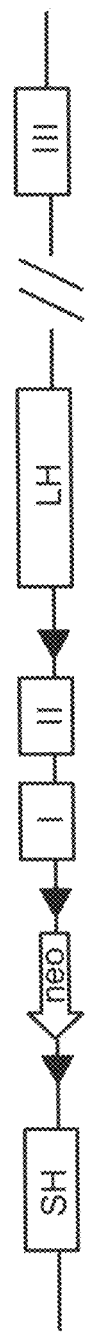
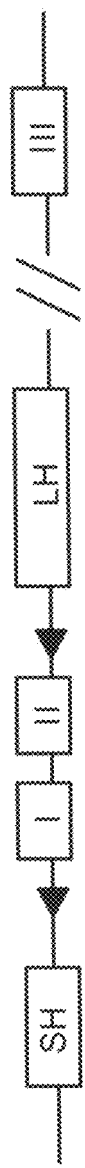
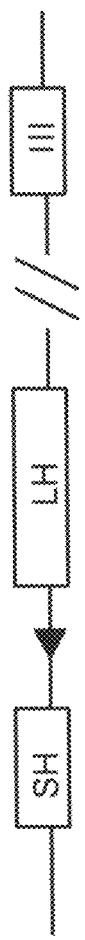
FIG. 1A
FIG. 1B
FIG. 1C

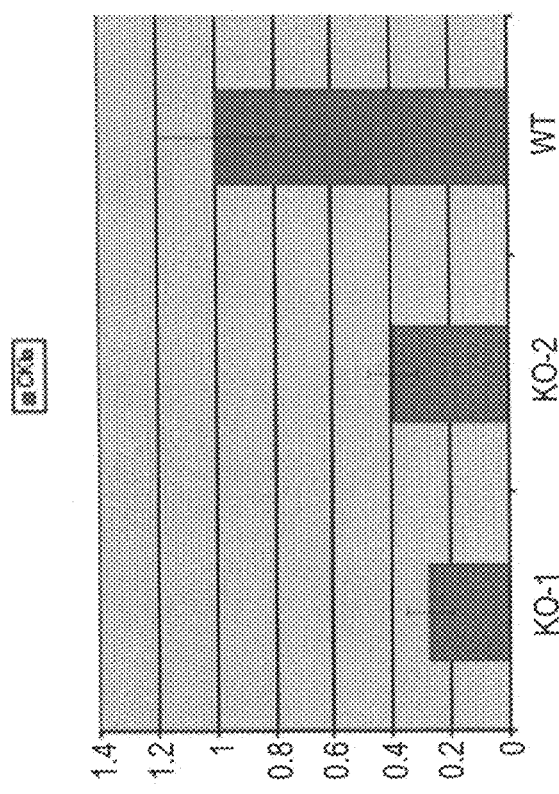
FIG. 2A
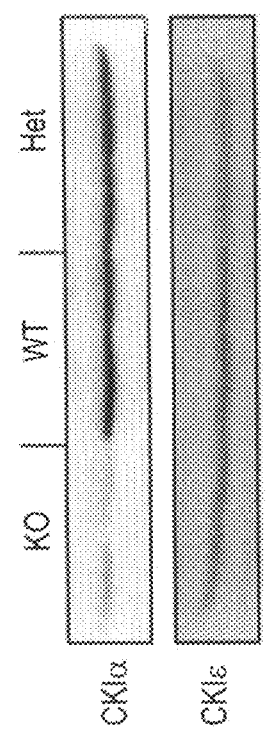
FIG. 2B
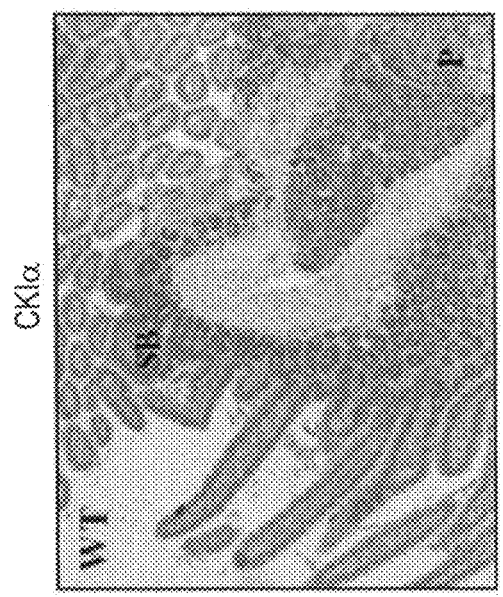
FIG. 2C

Cyclin D1

Cleaved caspase-3 p53

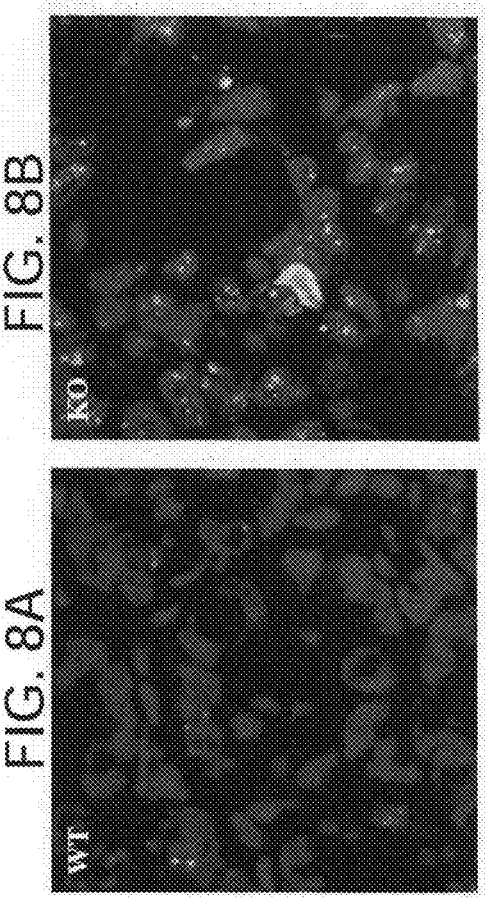
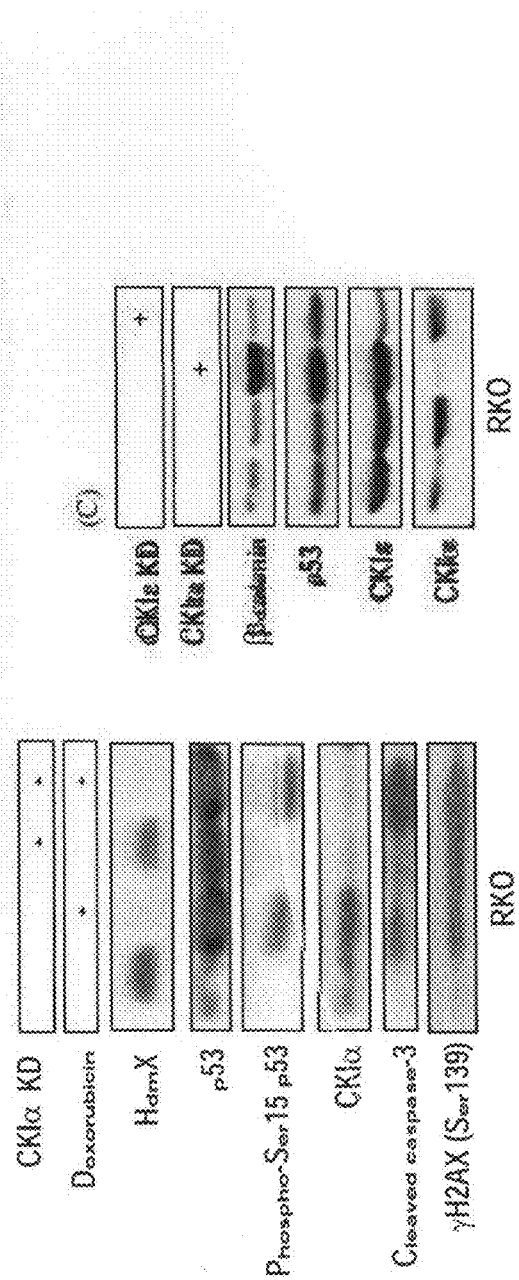
FIG. 8A
FIG. 8B
FIG. 8C
FIG. 8D

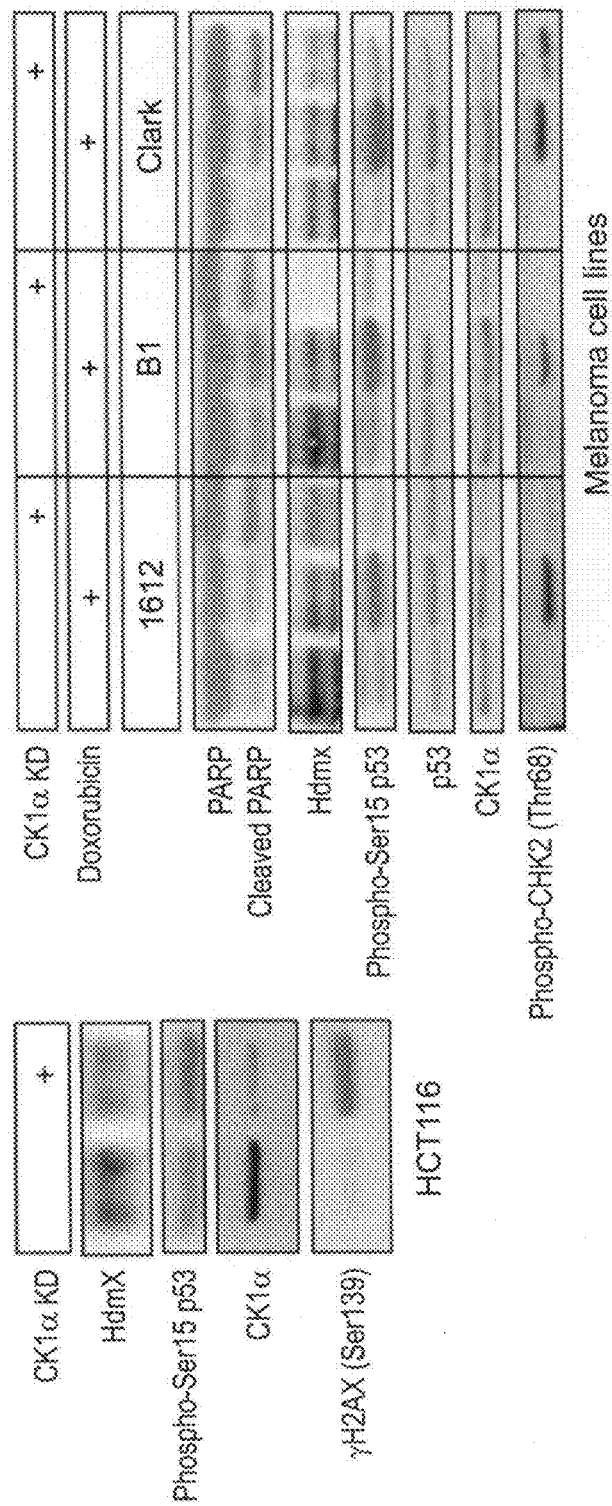

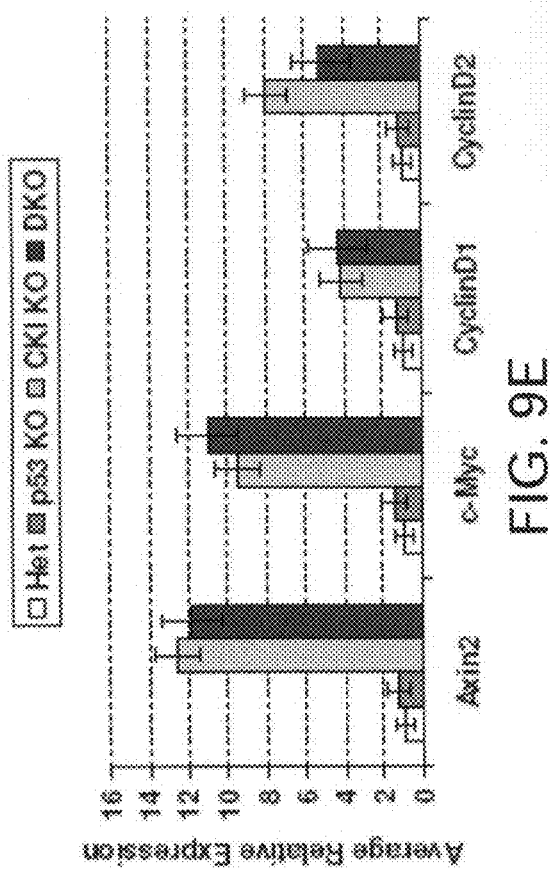
FIG. 9E
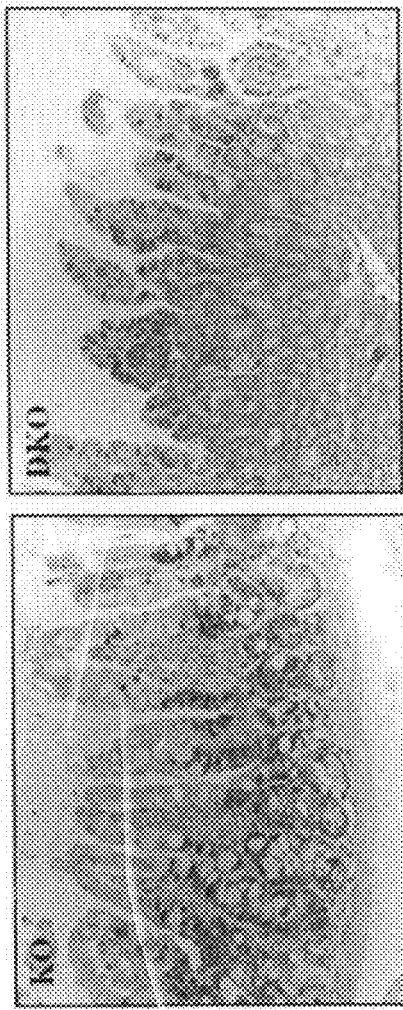
FIG. 9G
FIG. 9F

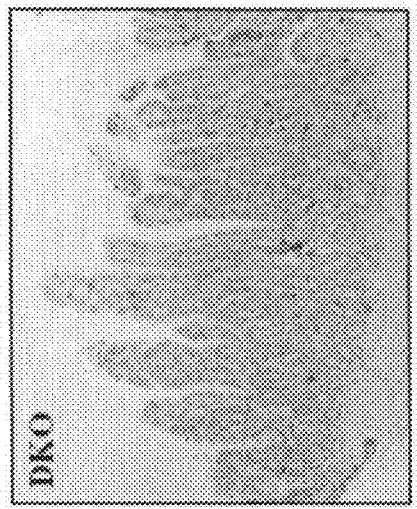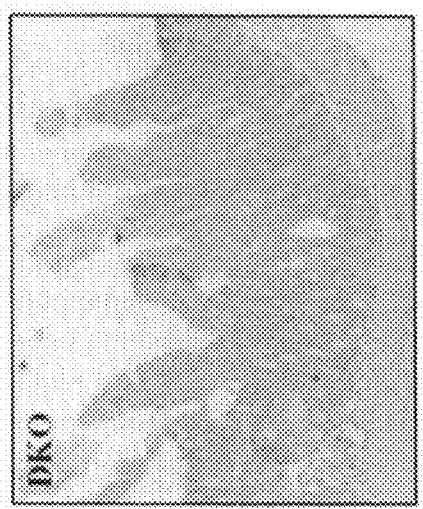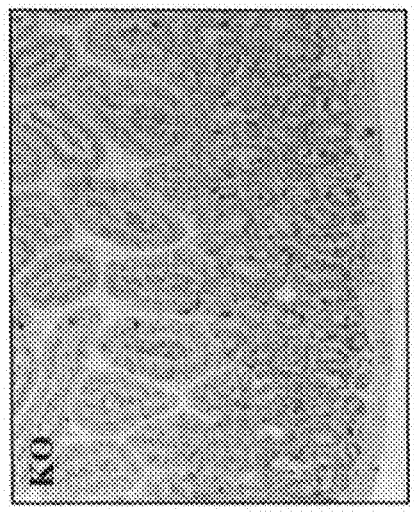

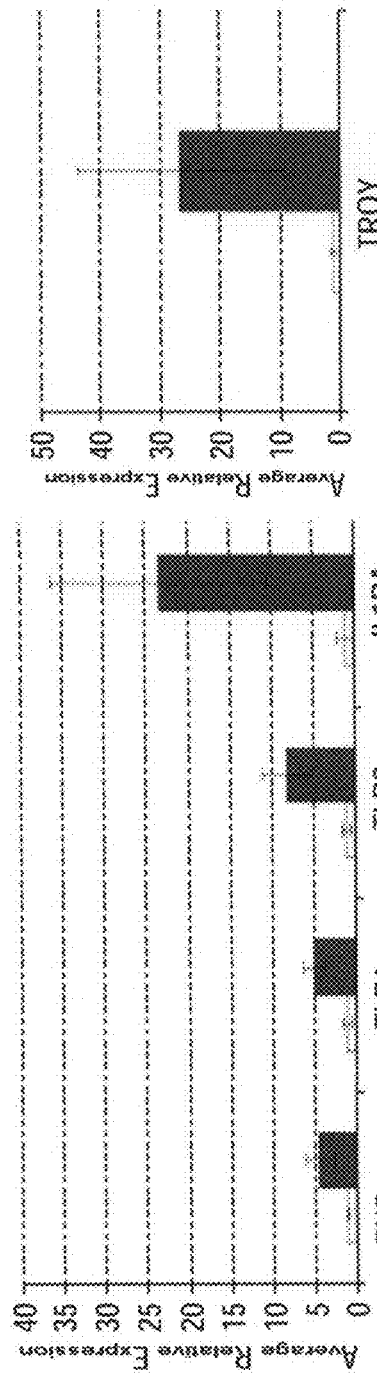
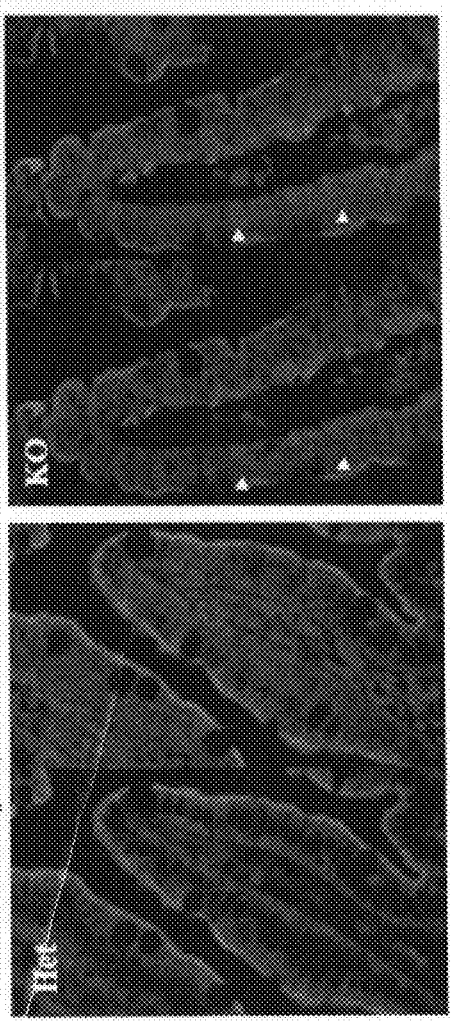
FIG. 12A
FIG. 12B
FIG. 12C
FIG. 12D

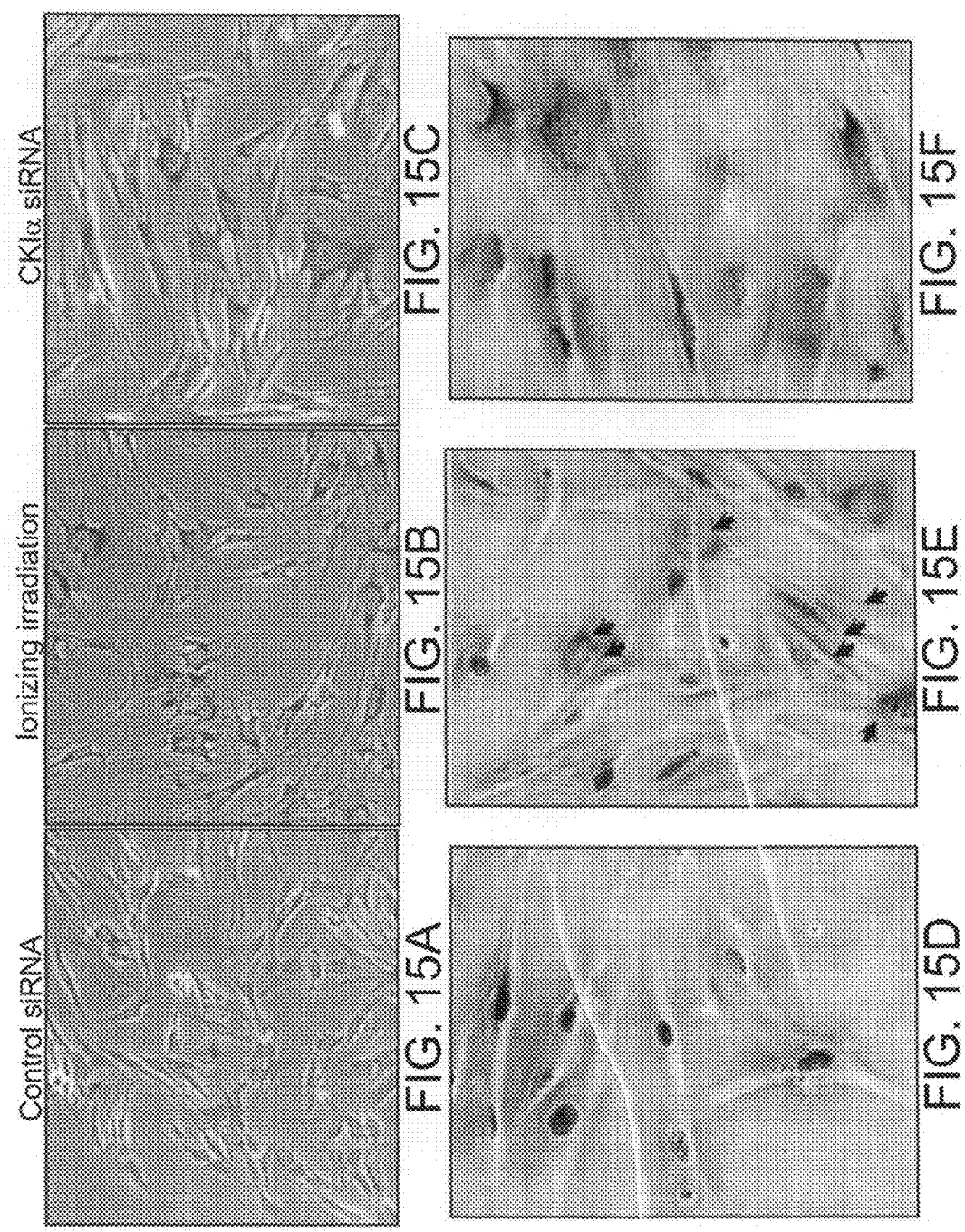

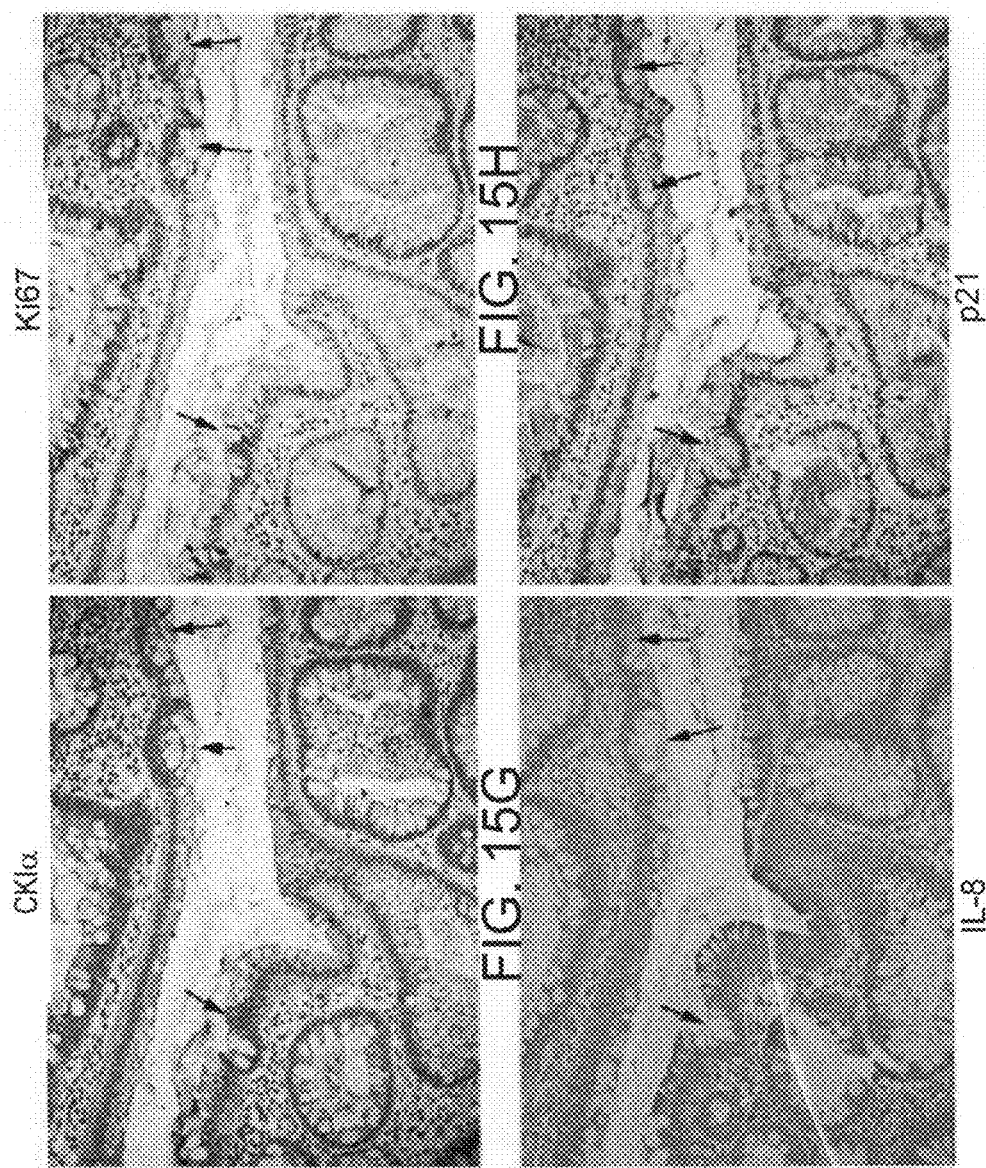

Cleaved caspase-3 p53

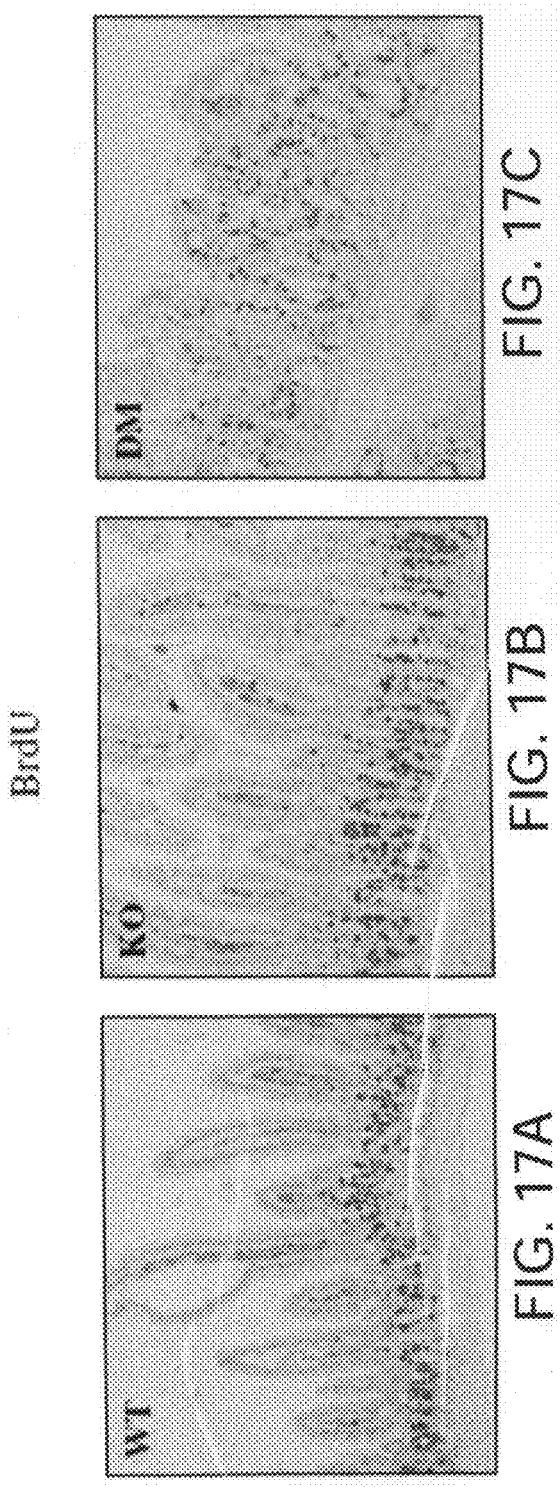

FIG. 18C
FIG. 18D

SEQUENCE LISTING

```
<160> NUMBER OF SEQ ID NOS: 6

<210> SEQ ID NO 1
<211> LENGTH: 64
<212> TYPE: DNA
<213> ORGANISM: Artificial sequence
<220> FEATURE:
<223> OTHER INFORMATION: Synthetic oligonucleotide used for cloning the
      CKI-alpha specific shRNA expression cassette

<400> SEQUENCE: 1 gatcccaag aagatgtcca cgcctgttca agagacaggc gtggacatct tcttttttg     60 gaaa                                                                64

<210> SEQ ID NO 2
<211> LENGTH: 64
<212> TYPE: DNA
<213> ORGANISM: Artificial sequence
<220> FEATURE:
<223> OTHER INFORMATION: Synthetic oligonucleotide used for cloning the
      CKI-alpha specific shRNA expression cassette

<400> SEQUENCE: 2
agcttttcca aaaaagaag atgtccacgc ctgtctcttg aacaggcgtg gacatcttct     60
tggg                                                                64

<210> SEQ ID NO 3
<211> LENGTH: 63
<212> TYPE: DNA
<213> ORGANISM: Artificial sequence
<220> FEATURE:
<223> OTHER INFORMATION: Synthetic oligonucleotide used for cloning the
      CKI-delta/epsilon specific shRNA expression cassette

<400> SEQUENCE: 3
gatcccgggc ttctcctatg actacttcaa gagagtagtc ataggagaag ccctttttgg    60
aaa                                                                 63

<210> SEQ ID NO 4
```

```
<211> LENGTH: 64
<212> TYPE: DNA
<213> ORGANISM: Artificial sequence
<220> FEATURE:
<223> OTHER INFORMATION: Synthetic oligonucleotide used for cloning the
      CKI-delta/epsilon specific shRNA expression cassette

<400> SEQUENCE: 4
agcttttcca aaagggctt ctcctatgac tactctcttg aagtagtcat aggagaagcc      60
cggg                                                                 64

<210> SEQ ID NO 5
<211> LENGTH: 57
<212> TYPE: DNA
<213> ORGANISM: Artificial sequence
<220> FEATURE:
<223> OTHER INFORMATION: Synthetic oligonucleotide used for cloning the
      CKI-delta specific shRNA expression cassette

<400> SEQUENCE: 5
ccggcccatc gaagtgttgt gtaaactcga gtttacacaa cacttcgatg ggttttt       57

<210> SEQ ID NO 6
<211> LENGTH: 21
<212> TYPE: DNA
<213> ORGANISM: Artificial sequence
<220> FEATURE:
<223> OTHER INFORMATION: An exemplary siRNA capable of down-regulating
      CKI-delta

<400> SEQUENCE: 6
gaaacauggu guccgguuut t                                              21
```

METHODS OF KILLING CELLS AND USE OF SAME IN PREVENTION AND TREATMENT OF CANCER

RELATED APPLICATIONS

This Application is a National Phase of PCT Patent Application No. PCT/IL2009/000526 having International filing date of May 26, 2009, which claims the benefit of U.S. Provisional Patent Application No. 61/071,947 filed on May 27, 2008. The contents of the above Applications are all incorporated herein by reference.

FIELD AND BACKGROUND OF THE INVENTION

The present invention relates to methods of killing cells by down-regulating CKI and use of same in prevention and treatment of cancer.

The Wnt pathway is highly conserved throughout evolution, from worms to man, playing crucial roles in embryonic development and diseases. Wnt signaling is strictly regulated by a set of kinases and phosphatases, acting on different components of the cascade and leading to various cell fates during an organism's life.

The main target of the canonical Wnt pathway is cytoplasmic β-catenin, which serves as a transcription co-activator for genes of proliferation, differentiation, migration and survival. The transduction of signal depends on the presence or absence of the Wnt ligand. In resting tissues, in the absence of Wnt ligand, β-catenin is constantly phosphorylated and degraded by a multiprotein complex, and is thus maintained at low levels in cells. In dividing cells, in adult's self-renewing tissues and throughout embryogenesis, secreted Wnt proteins bind to members of the Frizzled receptor family and to the coreceptor LRP5/6 on the cell membrane. Wnt binding activates Dishevelled (Dv1), resulting in dissociation of β-catenin degradation complex and stabilization of β-catenin in the cytoplasm. This enables the translocation of β-catenin into the nucleus and the activation of its target genes (e.g. c-Myc, cyclin D1) through Tcf/Lef-dependent transcription. Deregulation of the canonical Wnt signal leads to various cancers, among which is colorectal carcinoma (CRC), hepatocellular carcinoma (HCC) and melanoma. In such cancers, one or more Wnt component is often mutated, resulting in aberrant accumulation of nuclear β-catenin. This explains the requirement for tight regulation on β-catenin levels in the cell.

The mechanism by which β-catenin is phosphorylated and degraded has been revealed only recently, emphasizing significant players in the Wnt signaling pathway. The β-catenin degradation complex consists of the Adenomatous polyposis coli (APC) tumor suppressor, Axin1 or Axin2 (which are thought to play a scaffold function), and of two Serine/Threonine kinases: Casein kinase I (CKI) and Glycogen synthase kinase-3 (GSK3), which phosphorylate β-catenin on four N-terminal Ser/Thr residues. This event marks β-catenin for ubiquitination by the SCFP$^{β-TrCP}$ E3 ubiquitin ligase and subsequent proteasomal degradation. It has been shown lately that the first phosphorylation event is mediated by CKI, which phosphorylates Ser45 of β-catenin. This creates a priming site for GSK3, which subsequently phosphorylates Thr41, Ser37 and Ser33. The last two residues, when phosphorylated, serve as a docking site for the E3 ligase βTrCP, which marks β-catenin for degradation.

CKI's involvement was proven to be both necessary and sufficient for driving the cascade leading to β-catenin down-regulation. This is in agreement with studies on Wnt components' homologues in *Drosophila* and therefore assigns CKI as a Wnt antagonist. On the other hand, developmental studies in *Xenopus* and *C. elegans* implicated CKI as a Wnt effector, showing that CKI promotes secondary body axis and embryonic polarity (Wnt effects). Supporting that is the observation that CKI phosphorylates and activates Dv1, another Wnt effector, thereby increasing β-catenin levels.

CKI is a well-conserved family of Ser/Thr kinases found in every organism tested, from yeast to man. In mammals, the CKI family is composed of seven genes (α, β, $γ_1$, $γ_2$, $γ_3$, δ, ε) encoding 11 alternatively spliced isoforms. Members of the CKI family share a conserved catalytic domain and ATP-binding site, which exclusively differentiate them from other kinase families. CKI is a ubiquitous enzyme found in all cells, occupies different sub-cellular localizations and is involved in various cellular processes besides Wnt signaling.

Mutations in the canonical Wnt pathway abrogate its tight regulation resulting in nuclear accumulation of β-catenin, and the execution of an aberrant Wnt transcription program. These mutations occur in approximately 90% of colorectal cancers, as well as in other cancer types, such as hepatocellular carcinomas (HCC), gastric cancers and melanomas. Activating mutations in β-catenin itself have been reported in approximately 10% of colorectal cancers and up to 40% of HCC. Inactivating mutations in the Wnt pathway can occur in Axin1/2 genes and in the APC gene. Axin1 and Axin2 mutations have been found in HCC and colorectal cancer (CRC) respectively, though to a much lesser extent than APC mutations. The APC tumor suppressor gene is a primary target for somatic inactivating mutations in 85% of sporadic CRC's whereas in other types of cancer, APC mutations are rare. Thus the APC mutation, which was initially identified in the inherited cancer syndrome Familial Adenomatous Polyposis (FAP) is the major cause of sporadic CRC and is almost exclusive to this disease, i.e. APC is a colon-specific tumor suppressor gene.

The APC protein is a key regulator of the Wnt pathway. APC tumor suppressor has been shown to participate in several cellular processes including cell cycle regulation, apoptosis, cell adhesion, cell migration, signal transduction, microtubule assembly and chromosomal segregation. However, despite the fact that each of these roles are potentially linked to cancer, it appears that the tumor suppressing function of APC resides primarily in its capacity to properly regulate β-catenin. This effect takes place in two major posttranslational levels, enhancing β-catenin degradation and exporting it from the nucleus. In the absence of functional APC, β-catenin is stabilized and accumulates in the nucleus where it associates with members of the TCF/LEF family transcriptional activators, thus modulating transcription of Wnt target genes. Recent evidence also implicates APC in a nuclear role, suppressing β-catenin-mediated transcription by forming a repression complex on the DNA, thus giving it a third aspect of Wnt regulation.

Consistent with its tumor suppressing role, bi-allelic disruption of the APC gene occurs in both FAP and sporadic CRC. Inactivation of both APC alleles can be detected in most intestinal tumors at early stages of tumor development and the vast majority of APC mutations result in a truncated protein that lack Axin1/2 binding motifs and a varying number of the 20 amino acid repeats that are associated with β-catenin down-regulation.

Stöter et al [*Oncogene* (2005) 24, 7964-7975], teaches treatment of chiriocarcinomas with an inhibitor of CKI delta.

Yang, W S et al., Genome Biol. 2008; 9(6):R92. Epub 2008 Jun. 2 teaches treatment of cancer with inhibitors of CKI epsilon.

Behrend et al., [Oncogene, 9 Nov. 2000, Volume 19, Number 47, Pages 5303-5313] using specific inhibitors to CKI delta and epsilon teach that both these proteins are essential for an ordered mitotic progression.

U.S. Patent Application No. 20050171005 teaches treating colorectal cancer by providing compositions that up-regulate CKI.

U.S. Patent Application No. 20090005335 teaches treating cancer by providing compositions which down-regulate B-catenin.

SUMMARY OF THE INVENTION

According to an aspect of some embodiments of the present invention there is provided a method of killing a cell having a mutation in an Adenomatous polyposis coli (APC) gene, the method comprising contacting the cell with an inhibitor of Casein kinase I (CKI), said CKI being selected from the group consisting of CKIα and CKIδ, thereby killing the cell.

According to an aspect of some embodiments of the present invention there is provided a use of an inhibitor of CKI for the preparation of a medicament identified for the treatment of a cancer associated with a mutation in APC, said CKI being selected from the group consisting of CKIα, CKIδ and CKIε.

According to an aspect of some embodiments of the present invention there is provided a method of treating or preventing a cancer associated with a mutation in APC for onset and/or progression, in a subject in need thereof, the method comprising administering to the subject a therapeutically effective amount of an inhibitor of CKI, said CKI being selected from the group consisting of CKIα and CKIδ, thereby treating or preventing the cancer associated with a mutation in APC.

According to an aspect of some embodiments of the present invention there is provided a use of an inhibitor of CKIε and CKIδ for the preparation of a medicament identified for the treatment of cancer.

According to some embodiments of the invention, the cell is a colorectal cancer cell.

According to some embodiments of the invention, the cell is a medulloblastoma cell or a hepatocellular carcinoma cell.

According to some embodiments of the invention, the cell is heterozygous for said mutation in APC.

According to some embodiments of the invention, the cell is homozygous for said mutation in APC.

According to some embodiments of the invention, the inhibitor of CKI is selected from the group consisting of small chemical inhibitor and a polynucleotide inhibitor.

According to some embodiments of the invention, the inhibitor comprises an RNA silencing agent.

According to some embodiments of the invention, when the inhibitor is of CK1delta the method further comprises inhibiting CK1epsilon.

According to some embodiments of the invention, the cancer is colorectal cancer (CRC).

According to some embodiments of the invention, the cancer is a medulloblastoma or a hepatocellular cancer.

According to an aspect of some embodiments of the present invention there is provided a method of treating or preventing a cancer in a subject in need thereof, the method comprising administering to the subject a therapeutically effective amount of an inhibitor of CKIε and an inhibitor of CKIδ, thereby treating or preventing the cancer.

According to some embodiments of the invention, the cancer is associated with a mutation in APC for onset and/or progression.

According to some embodiments of the invention, the cancer is CRC or malignant melanoma.

According to an aspect of some embodiments of the present invention there is provided a pharmaceutical composition comprising as an active agent an inhibitor of CKIε and an inhibitor of CKIδ and a pharmaceutically acceptable carrier.

According to some embodiments of the invention, the pharmaceutical composition further comprises an inhibitor of CKIα.

According to an aspect of some embodiments of the present invention there is provided an article of manufacture comprising an inhibitor of CKIε and an inhibitor of CKIδ.

According to some embodiments of the invention, the article of manufacture further comprises an inhibitor of CKIα.

According to an aspect of some embodiments of the present invention there is provided a method of identifying and optionally producing an agent useful for treating a cancer associated with a mutation in APC for onset and/or progression, the method comprising:

(a) determining an activity or expression of CKI in a presence of the agent, said CKI being selected from the group consisting of CKIα and CKIδ;

(b) selecting the agent which down-regulates an activity or expression of said CKI, thereby identifying an agent useful for treating a cancer associated with a mutation in APC for onset and/or progression.

According to some embodiments of the invention, the method further comprises testing an effect of said candidate agent as a treatment for a cancer associated with a mutation in APC on a cancerous cell comprising a mutation in APC following step (b).

According to some embodiments of the invention, the method further comprises preparing a pharmaceutical composition containing said candidate agent identified by said testing.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The patent or application file contains at least one drawing executed in color. Copies of this patent or patent application publication with color drawing(s) will be provided by the Office upon request and payment of the necessary fee.

In the drawings:

Figure 3A:
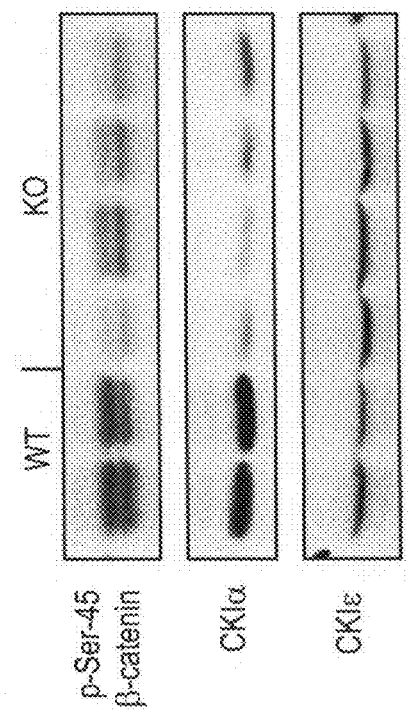

FIGS. 1A-C are diagrams illustrating CKIα targeting vector and knockout strategy. (A) A scheme of the CKIα targeting vector: short homology arm (SH); long homology arm (LH); exons (I, II, III); loxP sites (arrows); Neomycin resistance cassette (neo). (B) Conditional knockout allele, generated by transient Cre transfection in vitro, excising Neomycin resistance cassette. (C) Knockout allele, generated by cross to an inducible tissue-specific Cre mice in vivo, excising the first two exons of CKIα.

FIGS. 2A-C are photomicrographs and graphs illustrating CKIα expression in enterocytes isolated from small intestine epithelium. (A) Quantitative RT-PCR of CKIα transcript in two independent CKIα knockout (KO) mice and one wild-type (WT) mouse. (B) Western blot analysis of CKIα protein in two independent CKIα KO, WT and heterozygous (Het) mice. CKIε serves as loading control. (C) Immunohistochemistry of CKIα in WT and KO intestines. SB: small bowel; P: pancreas (control for tissue-specific deficiency).

FIGS. 3A-D are photographs illustrating that CKIα knockout induces β-catenin accumulation following its dephosphorylation. (A-B) Immunohistochemistry of β-catenin in WT and KO intestines. (C) Western blot analysis with specific antibody detecting phospho-Ser-45 of β-catenin in WT and KO enterocytes compared to CKIα levels. CKIε serves as loading control. (D) Western blot analysis of total β-catenin in WT and KO enterocytes compared to CKIα levels. PP2A-C is loading control.

FIGS. 4A-D are graphs and photographs illustrating the up-regulation of β-catenin target genes in CKIα KO mice. (A) Quantitative RT-PCR of Axin2, c-Myc, Cyclin D1 and Cyclin D2 in Heterozygous and KO mice (average values representing >4 mice in each group). (B) Western blot analysis of Cyclin D1 and D2 in Heterozygous and KO mice. Hsp90 is loading control. (C-D) Immunohistochemistry of Cyclin D1 in WT and KO mice.

FIGS. 5A-H are photographs and graphs illustrating apoptosis and p53 target genes induction in CKIα knockout mice. (A-D) Immunohistochemistry of cleaved Caspase-3 (A-B) and p53 (C-D) in small intestine of WT and KO. (E) Western blot analysis of p53 in enterocytes of WT and KO mice, compared to CKIα levels. PP2A-C is loading control (F) Quantitative RT-PCR of Bax and Cyclin G1 transcripts in heterozygous vs. KO mice (average values representing >4 mice in each group). (G) cDNA microarray analysis of Puma and Bax in two WT, two heterozygous and two KO mice. (H) Western blot analysis of Bax in enterocytes of heterozygous and KO mice, compared to CKIα levels. Hsp90 is loading control.

FIGS. 6A-G are photographs and graphs illustrating expression of p21 (Waf1/Cip1) upon CKIα ablation in mouse villi and human cells. (A-B) Immunohistochemistry of p21 in heterozygous and KO mice. (C) Western blot analysis of p21, compared to CKIα levels, in heterozygous and KO mice. Hsp90 is loading control. (D-G) Quantitative RT-PCR analysis of p21, Noxa, Puma and Bax in RKO cells transduced with lentiviral particles containing shRNA for CKIα and a non-relevant lentivirus (c1.1) as control.

Figure 7A:
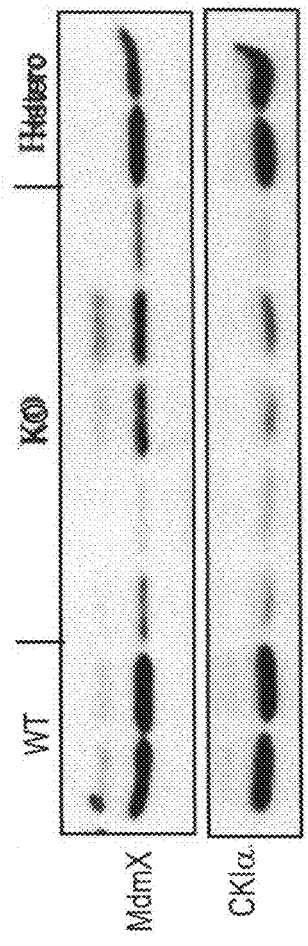
Figure 7B:
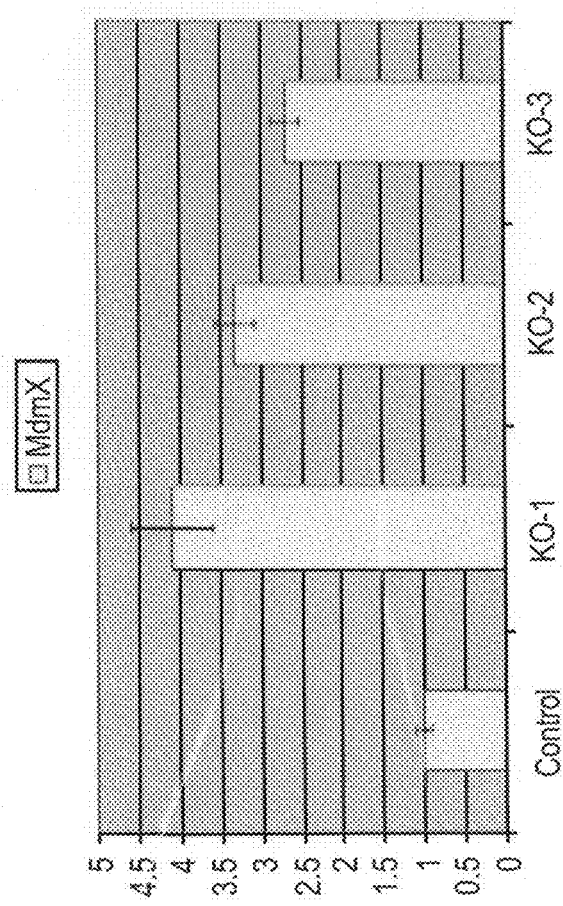

FIGS. 7A-B are graphs and photographs illustrating MdmX expression in enterocytes. (A) Western blot analysis of MdmX vs. CKIα levels in WT, KO and heterozygous mice. (B) Quantitative RT-PCR of MdmX in WT vs. three independent KO mice.

FIGS. 8A-F are photographs illustrating DNA damage response (DDR) and apoptosis upon CKIα ablation (A-B) Immunofluorescence of γH2A.X in an intestinal tissue of heterozygous and KO mice. Hoechst is a counterstain for nuclei. (C-F) Western blot analysis of DDR and apoptosis markers in human cell lines: (C) RKO colorectal carcinoma cells were transduced with lentiviral particles containing shRNA for CKIα (CKIα KD) or non relevant virus as control, treated with or without Doxorubicin (1 µg/ml), and assessed for activation of apoptosis and DNA damage, evident in p53 stabilization, cleaved caspase-3 activation and H2A.X phosphorylation, accordingly. (D) RKO cells were transduced with lentiviral particles containing shRNA for CKIα, CKIε and non relevant virus as control, and assessed for activation of p53 and β-catenin. (E) HCT116 colorectal carcinoma cells were transduced with lentiviral particles containing shRNA for CKIα and assessed for markers of DNA damage, evident in HdmX degradation, p53 phosphorylation at Ser15 and H2A.X phosphorylation. (F) Three different melanoma cell lines were transduced with lentiviral particles containing shRNA for CKIα, treated with or without Doxorubicin (1 µg/ml) and assessed for activation of apoptosis and DNA damage, evident in HdmX degradation, p53 elevation and PARP1 cleavage. Activation of the ATM pathway in 1612 cells is evident by phosphorylation of Chk2 at Thr68.

FIGS. 9A-H are graphs and photographs illustrating Wnt target gene expression in single CKIα KO and double CKIα/p53 KO. (A-B) Hematoxylin-Eosin (H&E) staining of CKIα KO (KO) and CKIα/p53 double KO (DKO) mice. (C-D) Immunohistochemistry of BrdU in KO and DKO mice. (E) Quantitative RT-PCR analysis of Axin2, c-Myc, Cyclin D1 and Cyclin D2 in heterozygous, p53 KO, CKIα KO and CKIα/p53 DKO mice (average values representing >4 mice in each group). (F-G) Immunohistochemistry of Cyclin D1 in CKIα KO and CKIα/p53 DKO mice. (H) Quantitative RT-PCR analysis of Bax, Cyclin G1, p21, Mdm2 and MdmX in heterozygous, p53 KO, CKIα KO and CKIα/p53 DKO mice (average values representing >4 mice in each group).

FIGS. 10A-D are photographs illustrating apoptosis and cell-cycle arrest in single CKIα KO and double CKIα/p53 KO. Immunohistochemistry of cleaved caspase-3 (A-B) and p21 (C-D) in CKIα KO and CKIα/p53 DKO mice.

Figures 11A, 11B:
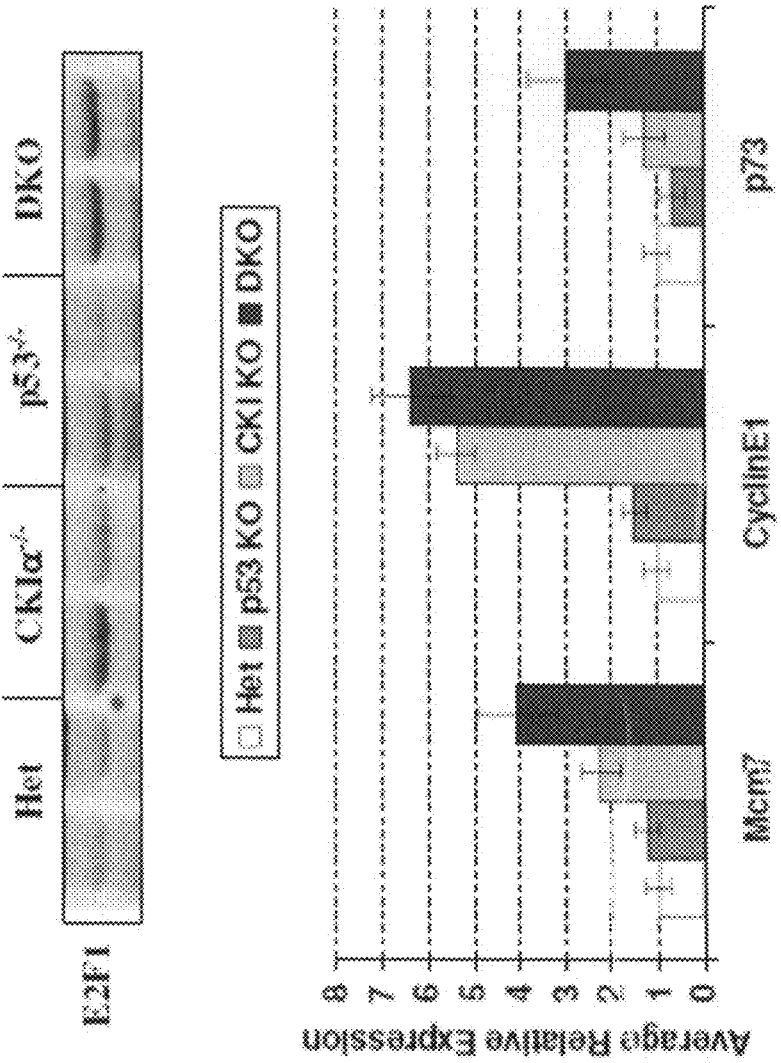

FIGS. 11A-B are photographs and graphs illustrating activation of the E2F1 pathway in single CKIα KO and double CKIα/p53 KO. (A) Western blot analysis of E2F1 in heterozygous, CKIα KO, p53 KO and CKIα/p53 DKO mice. (B) Quantitative RT-PCR analysis of the E2F1 target genes Mcm7, CyclinE1 and p73 in heterozygous, p53 KO, CKIα KO and CKIα/p53 DKO mice (average values representing >4 mice in each group).

FIGS. 12A-D are graphs and photographs illustrating that CKIα deficiency induces atypical inflammatory program. (A) Quantitative RT-PCR analysis of TNFα, TLR1, TLR2 and IL1RA in WT and heterozygous mice vs. CKIα KO mice (average values representing >4 mice in each group). (B) Quantitative RT-PCR analysis of Troy in WT and heterozygous mice vs. CKIα KO mice (average values representing >4 mice in each group). (C-D) Immunofluorescence of p65-NF-κB in heterozygous and KO mice (red), nuclei are counterstained with Hoechst (blue). Arrowheads indicate p65-positive nuclei.

FIGS. 13A-D are photographs illustrating that CKIα deletion induces a p53-independent senescence phenotype which is reversed by Sulindac. Senescence associated β-galactosidase (SA β-gal) assay on intestines of Het, CKIα KO, CKIα/p53 DKO and CKIα KO treated with Sulindac. Senesced cells accumulate β-gal which converts X-gal to a blue precipitate, red is nuclear counterstain (FastRed).

FIGS. 14A-I are graphs and photographs illustrating that Sulindac treatment prevents cell-non autonomous effects of CKIα deficiency. (A) Quantitative RT-PCR analysis of Cyclin D1 and c-Myc in Heterozygous mice vs. CKIα KO mice, with and without Sulindac in the drinking water (B) Western blot analysis of Cyclin D1 and p21 in heterozygous and CKIα KO with and without Sulindac. (C-H) Immunohistochemistry of Cyclin D1 (C-E) and p21 (F-H) in heterozygous, CKIα KO and CKIα KO treated with Sulindac. (I) Quantitative RT-PCR analysis of Troy, TLR2 and Cox2 in heterozygous mice vs. CKIα KO mice, with and without Sulindac.

FIGS. 15A-J are photographs illustrating that CKIα inhibition in human cells triggers senescence markers and DNA damage response. (A-C) SA-β-gal staining of IMR90 cells infected with control siRNA, treated with ionizing irradiation (positive control) and infected with CKIα siRNA (D-F) Double staining of γH2A.X and SA-β-gal in the same set of cells, showing full correlation between positive SA-β-gal and γH2A.X foci in irradiated and CKIα KD cells (G-J) Human intestinal polyps stained with CKIα, Ki67, IL-8 and p21, showing correlation between reduced CKIα expression, reduced Ki67 expression and induction of IL-8. Arrows indicate specific areas within the polyp, where CKIα is at high levels, Ki67 is highly expressed and IL-8 is downregulated.

FIGS. 16A-F are graphs and photographs illustrating an increased apoptosis in CKIα KO on a Min mouse background (double mutant mice). (A-D) Immunohistochemistry of cleaved caspase-3 (A-B) and p53 (C-D) in small intestine of CKIα KO and CKIα/Min double mutant (DM) mice. (E) Quantitative RT-PCR of Bax in control, KO, Min and DM mice. (F) Western blot analysis of Bax and MdmX in control, KO, Min and DM mice.

FIGS. 17A-C are photographs illustrating synergistic increase in proliferation upon CKIα deletion on a heterozygous Min mutant background. Immunohistochemistry of BrdU in WT, KO and DM mice that were injected with BrdU 2 hours prior to sacrifice.

FIGS. 18A-D are photographs and graphs illustrating synergistic upregulation of Cyclin D1 in double mutant mice. (A) Quantitative RT-PCR of Cyclin D1 in control, KO, Min and DM mice. (B) Western blot analysis of Cyclin D1 in control, KO, Min and DM mice. (C-D) Immunohistochemistry of Cyclin D1 in small intestine of KO and DM mice.

FIGS. 19A-G are photographs illustrating the characterization of adenomas in double mutant mice. (A-D) Immunohistochemistry of adenoma in DM mouse: H&E (A), CKIα (B), BrdU (C) and activated Caspase-3 (D). (E-G) Immunohistochemistry of an independent adenoma in a different DM mouse: H&E (E), CKIα (F) and Cyclin D1 (G).

FIGS. 20A-J are photographs illustrating that CKIδ KO and CKIδ/ε double KO induce DDR, apoptosis and p53-dependent cell cycle arrest. (A-F) H&E (A-B) and Immunohistochemistry of γH2A.X (C-D) and cleaved caspase-3 (E-F) in CKIδ KO and CKIδ/ε double KO mice. (G-J) Immunohistochemistry of p53 (G-H) and p21 (I-J) in CKIδ KO and CKIδ/ε double KO mice.

Figure 21:
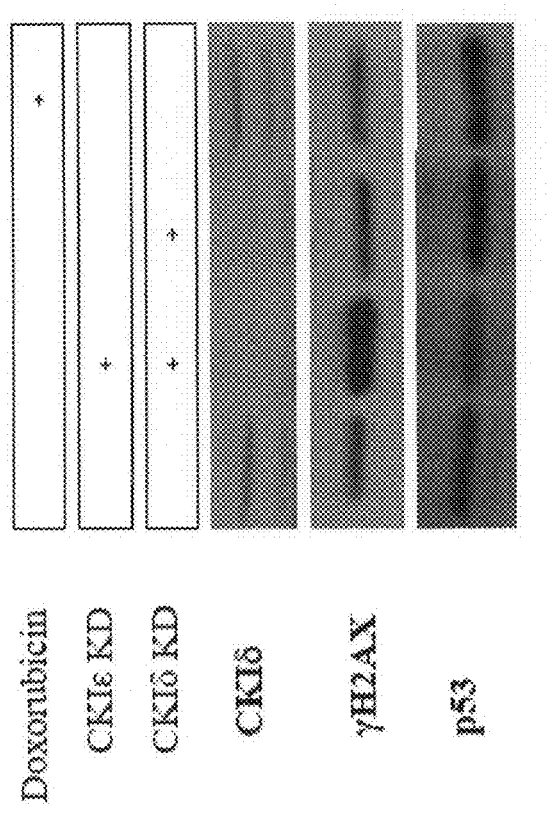

FIG. 21 is a photograph illustrating the DNA damage response (DDR) upon CKIδ/ε ablation. RKO colorectal carcinoma cells were transduced with lentiviral particles containing shRNA for CKIδ/ε or CKIδ alone (CKIδ/ε or CKIδ KD) or non-relevant virus as control, treated with or without Doxorubicin (1 μg/ml), and assessed for activation of DNA damage, evident by p53 stabilization and H2A.X phosphorylation.

DESCRIPTION OF THE PREFERRED EMBODIMENTS

The present invention is of methods of killing cells by down-regulating CKI and use of same in prevention and treatment of cancer.

The principles and operation of the method of killing cells according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The β-catenin degradation complex consists of the Adenomatous polyposis coli (APC) tumor suppressor, Axin1 or Axin2 (which are thought to play a scaffold function), and of two Serine/Threonine kinases: Casein kinase I (CKI) and Glycogen synthase kinase-3 (GSK3), which phosphorylate β-catenin on four N-terminal Ser/Thr residues. Both CKIα and APC are noted to play a role in Wnt signaling and mitotic spindle regulation.

In order to analyze the roles played by these two proteins, the present inventors generated mutant mice lacking CKIα in their intestinal epithelium, and also double mutant mice harboring villin-targeted CKIα deletion in combination with p53$^{-/-}$ or the APC$^{+/min}$ mutation.

Figure 9A:
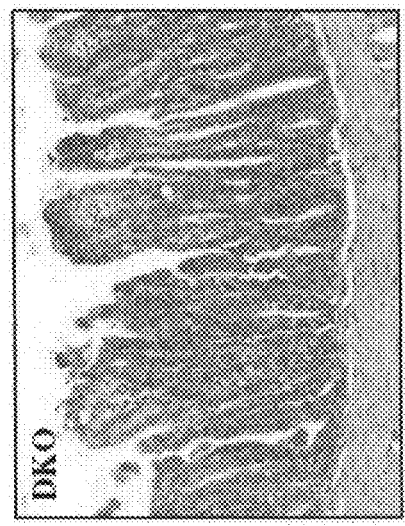
Figure 9B:
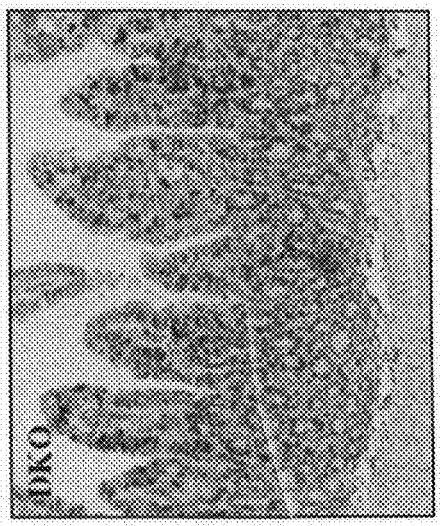
Figure 9C:
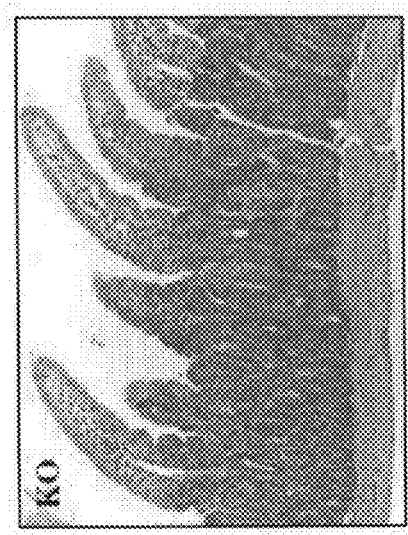

The present inventors found that CKIα intestinal knockout mice display a Wnt phenotype evident in nuclear accumulation of β-catenin (FIGS. 3A-D) in both crypts and villi and enhanced proliferation limited to the crypt (FIG. 9C). Nevertheless, no tumorigenic lesions (aberrant crypt foci or microadenomas) were evident in the CKIα mutant gut.

In accord, siRNA-mediated CKIα depletion in human colorectal carcinoma cell lines resulted in DDR, p53 activation and apoptosis (FIGS. 8C-E).

While, investigating the combined effect of CKIα deficiency and min mutation in the mouse gut, the present inventors surprisingly found that whereas CKIα-ablated mice are able to maintain the normal architecture and function of the small and large bowel and thrive normally, CKIα extinction in multiple intestinal neoplasias (min) mice (APC$^{+/min}$) resulted in serious gut pathology: widespread apoptosis accompanied by irregular compensatory proliferation (FIGS. 16A-F and 17A-C). Upon loss of CKIα, cells heterozygous for the APC$^{min}$ allele show dramatic upregulation of both p53 and p21, compared to single CKIα knockout mice. APC loss-of-heterozygosity cells mostly evade CKIα deletion, and the only aberrant crypt foci and microadenomas derive from deletion-spared CKIα positive tissue.

The present inventors conclude that the APC$^{+/min}$ mutation is incompatible with CKIα deficiency and the double mutation is synthetically lethal in intestinal epithelial cells.

On the basis of these observations the present inventors suggest that CKIα inhibition may eradicate intestinal epithelial cells harboring APC mutations, particularly APC-mutated tumors, without significantly compromising the normal gut epithelium and as such the present inventors propose that CKIα inhibitors may be used for the treatment of cancers associated with same.

Whilst further reducing the present invention to practice, the present inventors generated mutant mice lacking CKIδ, or ε, in their intestinal epithelium, either alone or in combination.

The present inventors found that that inhibition of CKIδ in the gut resulted in a DNA damage response (DDR) (FIGS. 20A-D), whereas co-inhibition of CKIδ and CKIε augmented this response and effectively blocked epithelial cell proliferation in the intestine (FIGS. 20A-J). In corroboration of these results, the present inventors found that siRNA-mediated mRNA depletion of both CKIδ and CKIε resulted in a pronounced DNA damage response in a human colorectal carcinoma cell line (FIG. 21).

On the basis of these observations, the present inventors propose that CKIδ inhibition, either alone or in combination with CKIε inhibition may be used as a treatment paradigm for the treatment of cancer.

Thus, according to an aspect of the present invention, there is provided a method of killing a cell having a mutation in an Adenomatous polyposis coli (APC) gene, the method comprising contacting the cell with an inhibitor of Casein kinase I (CKI), the CKI being selected from the group consisting of CKIα and CKIδ, thereby killing the cell.

The term "cell" as provided herein refers to a normal or diseased cell. Preferably the cell comprises a mutation (homozygous or heterozygous) in APC.

Examples of APC mutations are for instance those which cause truncation of the APC product. Typically mutations occur in the first half of the coding sequence, and somatic mutations in colorectal tumors are further clustered in a particular region, called MCR (mutation cluster region). List of APC mutations involved in human disease are provided in OMIM, www.ncbi.nlm.nih.gov/omim/ herein incorporated by reference in its entirety.

Methods of the present invention are effected by contacting/administering an agent capable of inhibiting CKI-alpha (CSNK1A; at the genomic, mRNA or protein level, GenBank Accession Nos. NP_001020276 and NM_001025105 and NM_001020276) and/or CKI-delta (CSNK1A; at the genomic, mRNA or protein level, GenBank Accession Nos. NP_001884.2, NP_620693.1, NM_001893.3 and NM_139062.1).

It will be appreciated that when the agent is one which inhibits CKI-delta, the present invention also contemplates contacting the cell with an inhibitor of CKI-epsilon (CSNK1E; NP_001885.1, NP_689407.1, NM_001894.4 NM_152221.2).

It will be further appreciated that the contacting is typically effected for a length of time and under suitable conditions such that the effect of the inhibitor is experienced.

Downregulation of CKI-alpha, CKI-delta and/or CKI-epsilon can be effected on the genomic and/or the transcript level using a variety of molecules that interfere with transcription and/or translation (e.g., antisense, siRNA, Ribozyme, micro RNA or DNAzyme), or on the protein level using, e.g., antagonists, enzymes that cleave the polypeptide, and the like.

The inhibitors may be specific for the particular CKI (i.e. CKI-alpha, delta or epsilon) or may have inhibitory activity towards more than one CKI (e.g. the same agent may comprise inhibitory activity towards both CKI delta and CKI epsilon).

Following is a non-comprehensive list of agents capable of downregulating expression level and/or activity of the CKIs of the present invention (CKI-alpha, CKI-delta and CKI-epsilon).

One example of an agent capable of downregulating the CKI's of the present invention is an antibody or antibody fragment capable of specifically binding the specific CKI. Preferably, the antibody specifically binds at least one epitope of CKI-alpha, CKI-delta or CKI-epsilon.

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three-dimensional structural characteristics, as well as specific charge characteristics.

Methods for humanizing non-human antibodies are well known in the art. Generally, a humanized antibody has one or more amino acid residues from a non-human source introduced into it. These non-human amino acid residues are often referred to as import residues, which are typically taken from an import variable domain. Humanization can be essentially performed following the method of Winter and co-workers (see Jones et al. (1986); Riechmann et al. (1988); and Verhoeyen, M. et al. (1988). Reshaping human antibodies: grafting an antilysozyme activity. Science 239, 1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom, H. R. and Winter, G. (1991). By-passing immunization. Human antibodies from synthetic repertoires of germline VH gene segments rearranged in vitro. J Mol Biol 227, 381-388). The techniques of Cole et al. and Boerner et al. are also available for the preparation of human monoclonal antibodies (Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Similarly, human antibodies can be made by introduction of human immunoglobulin loci into transgenic animals, e.g., mice, in which the endogenous immunoglobulin genes have been partially or completely inactivated. Upon challenge, human antibody production is observed to closely resemble that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; and 5,661,016; and in the following scientific publications: Marks, J. D. et al. (1992). By-passing immunization: building high affinity human antibodies by chain shuffling. Biotechnology (N.Y.) 10(7), 779-783; Lonberg et al., 1994. Nature 368:856-859;

Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93.

Another example of an agent capable of downregulating the CKIs of the present invention is an RNA silencing agent.

As used herein, the term "RNA silencing" refers to a group of regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

It will be appreciated that siRNA may be designed to inhibit more than one CKI (e.g. both CKI-delta and CKI-epsilon) by selecting sequences that are shared by both proteins. An exemplary siRNA capable of down-regulating CKI-alpha is as set forth in SEQ ID NOs: 1 and 2. An exemplary siRNA capable of down-regulating CKI-delta is as set forth in SEQ ID NO: 6 (5'-GAAACAUGGUGUC-CGGUUUTT-3). An exemplary siRNA capable of down-regulating CKI-epsilon is as set forth in SEQ ID NO: 5. An exemplary siRNA capable of down-regulating both CKI-delta and CKI-epsilon is set forth in SEQ ID NOs: 3 and 4.

Silencer RNAs for the CKIs of the present invention are also commercially available—for example from Applied Biosystems.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the CKI mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pls1, TAT(48-60), pVEC, MTS, and MAP.

Another agent capable of downregulating a CKI of the present invention is a DNAzyme molecule, which is capable of specifically cleaving an mRNA transcript or a DNA sequence of the CKI-alpha. DNAzymes are single-stranded polynucleotides that are capable of cleaving both single- and double-stranded target sequences (Breaker, R. R. and Joyce, G. F. (1995). A DNA enzyme with $Mg^{2+}$-dependent RNA phosphoesterase activity. Curr Biol 2, 655-660; Santoro, S. W. and Joyce, G. F. (1997). A general purpose RNA-cleaving DNA enzyme. Proc Natl Acad Sci USA 94, 4262-4266). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro and Joyce (1997)); for review of DNAzymes, see: Khachigian, L. M. (2002). DNAzymes: cutting a path to a new class of therapeutics. Curr Opin Mol Ther 4, 119-121.

Examples of construction and amplification of synthetic, engineered DNAzymes recognizing single- and double-stranded target cleavage sites are disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh, T. et al., Abstract 409, American Society of Gene Therapy 5th Annual Meeting (www.asgt.org), Jun. 5-9, 2002, Boston, Mass. USA.). In another application, DNAzymes complementary to bcr-abl oncogenes were successful in inhibiting the oncogene's expression in leukemia cells, and in reducing relapse rates in autologous bone marrow transplants in cases of Chronic Myelogenous Leukemia (CML) and Acute Lymphoblastic Leukemia (ALL).

Downregulation of the CKI of the present invention can also be effected by using an antisense polynucleotide capable of specifically hybridizing with an mRNA transcript encoding the CKI.

Design of antisense molecules that can be used to efficiently downregulate a CKI must be effected while considering two aspects important to the antisense approach. The first aspect is delivery of the oligonucleotide into the cytoplasm of the appropriate cells, while the second aspect is design of an oligonucleotide that specifically binds the designated mRNA within cells in a manner inhibiting the translation thereof.

The prior art teaches of a number of delivery strategies which can be used to efficiently deliver oligonucleotides into a wide variety of cell types (see, for example: Luft, F. C. (1998). Making sense out of antisense oligodeoxynucleotide delivery: getting there is half the fun. J Mol Med 76(2), 75-76 (1998); Kronenwett et al. (1998). Oligodeoxyribonucleotide uptake in primary human hematopoietic cells is enhanced by cationic lipids and depends on the hematopoietic cell subset. Blood 91, 852-862; Rajur, S. B. et al. (1997). Covalent protein-oligonucleotide conjugates for efficient delivery of antisense molecules. Bioconjug Chem 8, 935-940; Lavigne et al. Biochem Biophys Res Commun 237: 566-71 (1997); and Aoki, M. et al. (1997). In vivo transfer efficiency of antisense oligonucleotides into the myocardium using HVJ-liposome method. Biochem Biophys Res Commun 231, 540-545).

In addition, also available are algorithms for identifying those sequences with the highest predicted binding affinity for their target mRNA based on a thermodynamic cycle that accounts for the energetics of structural alterations in both the target mRNA and the oligonucleotide (see, for example, Walton, S. P. et al. (1999). Prediction of antisense oligonucleotide binding affinity to a structured RNA target. Biotechnol Bioeng 65, 1-9).

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF-alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiencies of specific oligonucleotides using an in vitro system were also published (Matveeva, O. et al. (1998). Prediction of antisense oligonucleotide efficacy by in vitro methods. Nature Biotechnology 16, 1374-1375).

Several clinical trials have demonstrated the safety, feasibility, and activity of antisense oligonucleotides. For example, antisense oligonucleotides suitable for the treatment of cancer have been successfully utilized (Holmund, B. P. et al. (1999). Toward antisense oligonucleotide therapy for cancer: ISIS compounds in clinical development. Curr Opin Mol Ther 1, 372-385), while treatment of hematological malignancies via antisense oligonucleotides targeting c-myb gene, p53, and Bcl-2 entered clinical trials and was shown to be tolerated by patients (Gewirtz, A. M. (1999). Oligonucleotide therapeutics: clothing the emperor. Curr Opin Mol Ther 1, 297-306).

More recently, antisense-mediated suppression of human heparanase gene expression was reported to inhibit pleural dissemination of human cancer cells in a mouse model (Uno, F. et al. (2001). Antisense-mediated suppression of human heparanase gene expression inhibits pleural dissemination of human cancer cells. Cancer Res 61, 7855-7860).

Thus, the current consensus is that recent developments in the field of antisense technology, which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a CKI is a ribozyme molecule capable of specifically cleaving an mRNA transcript encoding the specific CKI. Ribozymes increasingly are being used for the sequence-specific inhibition of gene expression by the cleavage of mRNAs encoding proteins of interest (Welch, P. J. et al. (1998). Expression of ribozymes in gene transfer systems to modulate target RNA levels. Curr Opin Biotechnol 9, 486-496). The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers, and specific somatic mutations in genetic disorders (Welch, P. J. et al. (1998). Ribozyme gene therapy for hepatitis C virus infection. Clin Diagn Virol 10, 163-171). Most notably, several ribozyme gene therapy protocols for HIV patients are already in Phase 1 trials. More recently, ribozymes have been used for transgenic animal research, gene target validation, and pathway elucidation. Several ribozymes are in various stages of clinical trials. ANGIOZYME™ was the first chemically synthesized ribozyme to be studied in human clinical trials. ANGIOZYME specifically inhibits formation of the VEGFR (Vascular Endothelial Growth Factor receptor), a key component in the angiogenesis pathway. Ribozyme Pharmaceuticals, Inc., as well as other firms, has demonstrated the importance of anti-angiogenesis therapeutics in animal models. HEPTAZYME™, a ribozyme designed to selectively destroy Hepatitis C Virus (HCV) RNA, was found effective in decreasing Hepatitis C viral RNA in cell culture assays (Ribozyme Pharmaceuticals, Inc., Boulder, Colo., USA (www.rpi.com)).

An additional method of regulating the expression of a CKI gene in cells is via triplex-forming oligonucleotides (TFOs). Recent studies show that TFOs can be designed to recognize and bind to polypurine or polypyrimidine regions in double-stranded helical DNA in a sequence-specific manner. These recognition rules are outlined in: Maher III, L. J., et al. (1989). Inhibition of DNA binding proteins by oligonucleotide-directed triple helix formation. Science 245, 725-730; Moser, H. E., et al. (1987). Sequence-specific cleavage of double helical DNA by triple helix formation. Science 238, 645-650; Beal, P. A. and Dervan, P. B. (1991). Second structural motif for recognition of DNA by oligonucleotide-directed triple-helix formation. Science 251, 1360-1363; Cooney, M., et al. (1988). Science 241, 456-459; and Hogan, M. E., et al., EP Publication 375408. Modifications of the oligonucleotides, such as the introduction of intercalators and backbone substitutions, and optimization of binding conditions (e.g., pH and cation concentration) have aided in overcoming inherent obstacles to TFO activity such as charge repulsion and instability, and it was recently shown that synthetic oligonucleotides can be targeted to specific sequences (for a recent review, see Seidman, M. M. and Glazer, P. M. (2003). The potential for gene repair via triple helix formation J Clin Invest 112, 487-494).

In general, the triplex-forming oligonucleotide has the sequence correspondence:

| oligo | 3'--A | G | G | T |
| duplex | 5'--A | G | C | T |
| duplex | 3'--T | C | G | A |

However, it has been shown that the A-AT and G-GC triplets have the greatest triple-helical stability (Reither, S. and Jeltsch, A. (2002). Specificity of DNA triple helix formation analyzed by a FRET assay. BMC Biochem 3(1), 27, Epub). The same authors have demonstrated that TFOs designed according to the A-AT and G-GC rule do not form nonspecific triplexes, indicating that triplex formation is indeed sequence-specific.

Thus, a triplex-forming sequence may be devised for any given sequence in the CKI regulatory region. Triplex-forming oligonucleotides preferably are at least 15, more preferably 25, still more preferably 30 or more, nucleotides in length, up to 50 or 100 bp.

Transfection of cells with TFOs (for example, via cationic liposomes) and formation of the triple-helical structure with the target DNA induces steric and functional changes, blocking transcription initiation and elongation, allowing the introduction of desired sequence changes in the endogenous DNA, and resulting in the specific downregulation of gene expression. Examples of suppression of gene expression in cells treated with TFOs include: knockout of episomal supFG1 and endogenous HPRT genes in mammalian cells (Vasquez, K. M. et al. (1999). Chromosomal mutations induced by triplex-forming oligonucleotides in mammalian cells. Nucl Acids Res 27, 1176-1181; and Puri, N. et al. (2001). Targeted Gene Knockout by 2'-O-Aminoethyl Modified Triplex Forming Oligonucleotides. J Biol Chem 276, 28991-28998); the sequence- and target-specific downregulation of expression of the Ets2 transcription factor, important in prostate cancer etiology (Carbone, G. M. et al., Selective inhibition of transcription of the Ets2 gene in prostate cancer cells by a triplex-forming oligonucleotide. Nucl Acids Res 31, 833-843); and regulation of the pro-inflammatory ICAM-1 gene (Besch, R. et al. (2003). Specific inhibition of ICAM-1 expression mediated by gene targeting with Triplex-forming oligonucleotides. J Biol Chem 277, 32473-32479). In addition, Vuyisich and Beal have recently shown that sequence-specific TFOs can bind to dsRNA, inhibiting activity of dsRNA-dependent enzymes such as RNA-dependent kinases (Vuyisich, M. and Beal, P. A. (2000). Regulation of the RNA-dependent protein kinase by triple helix formation. Nucl Acids Res 28, 2369-2374).

Additionally, TFOs designed according to the abovementioned principles can induce directed mutagenesis capable of effecting DNA repair, thus providing both downregulation and upregulation of expression of endogenous genes (Seidman and Glazer (2003)). Detailed description of the design, synthesis, and administration of effective TFOs can be found in U.S. patent application Ser. Nos. 03/017,068 and 03/009,6980 to Froehler et al. and Ser. Nos. 02/012,8218 and 02/012,3476 to Emanuele et al., and U.S. Pat. No. 5,721,138 to Lawn.

MicroRNAs can be designed using the guidelines found in the art. Algorithms for design of such molecules are also available. See e.g., www.wmddotweigelworlddotorg/cgi-bin/mirnatoolsdotpl, herein incorporated by reference.

Another agent capable of downregulating the CKIs of the present invention is any molecule which binds to and/or cleaves the CKI. Such molecules can be, for instance, CKI antagonists, or a CKI inhibitory peptide.

It will be appreciated that a non-functional analogue of at least a catalytic or binding portion of CKI can be also used as an agent which downregulates CKI.

Small chemical CKI inhibitors are also contemplated by the present invention. These chemical agents may have selective inhibitory activities towards one particular CKI or may comprise inhibitory activities towards two or more CKIs. For example, IC261 (available from Santa Cruz technology) is a specific inhibitor of the CKI-delta and CKI-epsilon.

Another agent that can be used according to the present invention to downregulate CKI is a molecule which prevents CKI activation or substrate binding.

Other agents which may be used to regulate CKI-alpha, delta or epsilon can be found or refined (for enhanced selectivity, specificity) using screening methods which are well known in the art. Examples of such assays include biochemical assays (e.g., in-vitro kinase activity), cell biology assays (e.g. protein localization) and molecular assays (e.g., Northern, Western and Southern blotting).

Below is a description of various assays that may be used to screen small chemical agents for the ability to downregulate one of the CKIs of the present invention.

Enzyme Inhibition Assays:
1. Incubate recombinant CKIepsilon enzyme with a small molecule inhibitor (SMI) for 10 minutes; add the substrate human Per2 and observe Ser662 phosphorylation by protein upshift on SDS-PAGE (Toh et al, Science 291:1040, 2001).

2. Incubate recombinant CKIdelta enzyme with an SMI for 10 minutes; add the substrate mouse p53 and observe Thr18 phosphorylation by Western blotting using Novus Rabbit Anti-p53, phospho (Thr18) Polyclonal Antibody (NB100-92607).
3. Incubate human tumor cells with an SMI for 1-24 hours; harvest the cells and analyze them for beta-catenin phosphorylation on Ser45 with Invitrogen Rabbit Anti-beta-Catenin, phospho (Ser45) Polyclonal Antibody (44-208G) (a unique property of CKIalpha)

Biological Assays

1. Incubate human tumor cells with an SMI for 1-24 hours; harvest the cells and analyze them for DDR and p53 activation with antibodies to γH2A.X and p53 by immunohistochemistry or Western Blotting.
2. Incubate human primary tumor cells and tumor-associated fibroblasts with an SMI for 24 hours; remove the SMI and replacing the culture medium; analyze the cells for cellular senescence by Senescence-Associated β-galactosidase assay (SA-β-Gal).

Candidate agents may include, small chemical inhibitors, antibodies or various polynucleotide agents such as those described herein above. Following identification using the screening methods listed above, the agents may be tested as a candidate anti-cancer agent on cancerous cells (e.g. cancerous cells comprising a mutation in APC). Confirmation of an anti-cancer agent may be followed by preparation of a pharmaceutical composition comprising same as detailed herein below.

Polypeptide agents (e.g. antibodies) and chemical agents for downregulating the CKIs of the present invention may be provided to the cells per se. Polynucleotide agents or small peptide agents are typically administered to cells as part of an expression construct. In this case, the polynucleotide agent is ligated in a nucleic acid construct under the control of a cis-acting regulatory element (e.g. promoter). The promoter may be capable of directing an expression of the agent in a constitutive or inducible manner. The promoter may also be tissue-specific. An exemplary promoter that is specific to the gut is the promoter associated with Villin. The present invention also contemplates use of a metastic colon cancer specific promoter, such as described in U.S. Pat. No. 7,364,727.

The nucleic acid construct may be introduced into the cells using an appropriate gene delivery vehicle/method (transfection, transduction, etc.) and an appropriate expression system. Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www-.invitrogen.com). Lipid-based systems may be used for the delivery of these constructs into the expanded adult islet beta cells of the present invention. Useful lipids for lipid-mediated transfer of the gene are, for example, DOTMA, DOPE, and DC-Chol [Tonkinson et al., Cancer Investigation, 14(1): 54-65 (1996)]. Recently, it has been shown that Chitosan can be used to deliver nucleic acids to the intestine cells (Chen J. (2004) World J Gastroenterol 10(1):112-116). Other non-lipid based vectors that can be used according to this aspect of the present invention include but are not limited to polylysine and dendrimers.

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lenti viral vectors and herpesviral vectors.

A viral construct such as a retroviral construct includes at least one transcriptional promoter/enhancer or locus-defining element(s), or other elements that control gene expression by other means such as alternate splicing, nuclear RNA export, or post-transcriptional modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the peptide variants of the present invention. Optionally, the construct may also include a signal that directs polyadenylation, as well as one or more restriction site and a translation termination sequence. By way of example, such constructs will typically include a 5' LTR, a tRNA binding site, a packaging signal, an origin of second-strand DNA synthesis, and a 3' LTR or a portion thereof.

Preferably the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

Since the CKI inhibitors of the present invention were shown to be effective at eradicating intestinal epithelial cells harboring APC mutations, the present invention contemplates treatment or prevention of a cancer associated with a mutation in APC for onset and/or progression using such inhibitors.

Examples of diseases which may involve APC mutations include, but are not limited to, malignant diseases (such as colorectal cancer, medulloblastoma, hepatocellular carcinoma) as well as other syndromes which include Turcot syndrome and hereditary desmoid disease.

As mentioned, the present invention also contemplates treating subjects with other cancers with a combination of two inhibitors one which down-regulates CKI-delta and the other which down-regulates CKI-epsilon. Additionally, the present invention contemplates treating subjects with other cancers with an agent that comprises inhibitory activity towards both CKI-delta and CKI-epsilon.

Specific examples of cancers which can be treated using inhibitors of CKI-delta and CKI-epsilon of the present invention include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma; lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma;

osteosarcoma; ovarian cancer; ovarian cancer, serous; ovarian carcinoma; ovarian sex cord tumors; pancreatic cancer; pancreatic endocrine tumors; paraganglioma, familial non-chromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

Each of the downregulating agents described hereinabove or the expression vector encoding CKI inhibitors may be administered to the individual per se or as part of a pharmaceutical composition, which also includes a physiologically acceptable carrier. The purpose of a pharmaceutical composition is to facilitate administration of the active ingredient to an organism.

As used herein a "pharmaceutical composition" refers to a preparation of one or more (e.g. a CKI-delta inhibitor and a CKI-epsilon inhibitor) of the active ingredients described herein with other chemical components such as physiologically suitable carriers and excipients.

Herein the term "active ingredient" refers to the agent (e.g., silencing molecule) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue. In an exemplary embodiment the tissue is a colon cancer tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models (e.g., the APC model exemplified herein) to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The kit may comprise a combination of the inhibitors, such as a CKI-delta inhibitor and a CKI-epsilon inhibitor. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N. Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Plasmids and ES Culture:

CKIα vector was constructed on the basis of pGEM 11 Zf (+), to which an XbaI/SalI fragment of neomycin-LoxP cassette was inserted from pL2neo expression vector. Exons 1 and 2 of CKIα were flanked by LoxP sites. CKIδ and CKIε vectors were constructed on the basis of pEZ FrtLox DT. Exon 3 of CKIδ and exons 3 and 4 of CKIε were flanked by LoxP sites. Genomic fragments were amplified by PCR from 129/SVJ mouse DNA. The vectors were linearized with SalI (CKIα) and SfiI (CKIδ/ε) and cleaned using phenol-chloroform and ethanol precipitation methods. Electroporation was done using BioRad electroporator and an electroporation buffer (Sigma) into R1 ES cells. ES cell culture was grown on feeder layer of mouse embryonic fibroblasts (mEF) using DMEM supplemented with 15% ES-tested FBS and 1000 units/ml ESGRO (Chemicon). Neomycin selection was performed in 0.2 mg/ml G-418. For CKIα clones, pCA NLS-Cre was used as a Cre expression vector for transient transfection of Cre in ES cells. Selection was performed in 2 μg/ml puromycin.

Aggregation, Mice Breeding and Genotyping:

R1 positive clone (agouti) was aggregated to ICR morulas (white) using morula aggregation method and chimerism was detected by a mixed coat color of the chimeric mice. ICR mice (Weizmann Institute) were used as background to check for germ-line transmission. Rosa-Frt mice were used to excise the neo cassette in CKIδ and CKIε vectors. Villin-Cre-ER$^{T2}$ mice (C57BL/6 background) were used to delete floxed CKIα in vivo, conditionally in gut epithelium.

Tamoxifen Treatment and Tissue Preparation:

Tamoxifen (Sigma) was dissolved in Corn Oil (Sigma) to a 20 mg/ml concentration. Mice at 2-3 months were injected subcutaneously with 2 mg Tamoxifen per injection, 5-7 injections every other day, over a 10-14 day period. Mice were sacrificed 4-5 days after the last injection. The colon and part of the small intestine were taken for histology, together with the stomach, liver, pancreas, spleen, kidney, heart and lung. Enterocytes (intestinal epithelial cells) were isolated from most of the small intestine. Enterocytes were used for RNA and protein assays.

Histology, Immunohistochemistry and BrdU Labeling:

All tissues were fixated in 4% formaldehyde for 24 hours, paraffin embedded and sectioned at 5 μm for hematoxylin/eosin (H&E) staining and immunohistochemistry. BrdU (Amersham) was injected intraperitonally at 100 μl/10 g body weight, 2 hours prior to sacrifice. The primary antibodies used were goat anti-CKIα (1:100; Santa Cruz), rabbit anti-Cleaved Caspase-3 (1:100; Cell Signaling), rabbit CM5 (anti-mouse p53) (1:400; Novocastra), mouse anti-β-catenin (1:200; BD transduction), mouse anti-BrdU (1:100; NeoMarkers), rabbit anti-Cyclin D1 (1:125; Lab Vision), mouse anti-p21 (1:50; Santa Cruz), mouse anti-γH2AX (Ser139) (1:100; Upstate), mouse anti-IL-8 (1:125; Bender), rabbit anti-Ki67 (1:300; NeoMarkers). The secondary antibodies used for immunohistochemistry were HRP-polymer anti-Rabbit and anti-Goat (Nichirei), HRP-polymer Mouse on Mouse kit (Nichirei), Mach2 anti mouse-HRP polymer (Biocare) and Mouse-Envision Plus (Dako). HRP was visualized with DAB chromogen (Thermo Scientific) and nuclear counterstain was hemotoxylin (BioOptica). The secondary antibody used for immunofluorescence was goat anti mouse Alexa-488 (1:1000; Molecular Probes). The nuclear counterstain used for immunofluorescence was Hoechst (1.5 μg/ml, Molecular Probes).

Intestinal Cell Preparation, Western Blotting and RNA Analysis:

For enterocyte isolation, ~⅔ of the small intestine was washed and minced into small pieces in PBS/1 mM DTT. Intestine was separated into single cells in $Ca^{2+}$, $Mg^{2+}$ free HBSS containing 10 mM HEPES, 5 mM EDTA and 0.5 mM DTT, at 37° C. for 30 minutes with slow agitation. Lysate was mixed vigorously and cell suspension was centrifuged. Cell pellets were frozen in liquid $N_2$ and stored at −80° C. Protein was extracted from cell pellets in cell lysis buffer containing protease and phosphatase inhibitors. Primary antibodies used in Western blotting were goat-anti CKIα (1:100; Santa Cruz), mouse anti-CKIε (1:250; Santa Cruz), mouse anti-β-catenin (1:2500; BD transduction), rabbit anti-Phospho-β-catenin (Thr41/Ser45) (1:750, Cell Signaling), rabbit CM5 (anti-mouse p53) (1:400; Novocastra), mouse anti-human p53 (1:20; DO-1 hybridoma), rabbit anti-Phospho-p53 (Ser15) (1:1000; Cell Signaling), rabbit anti-Cyclin D1 (1:300; Lab Vision), rabbit anti-Cyclin D2 (1:1000; Santa Cruz), rabbit-anti Bax (1:200; Santa Cruz), mouse anti-MdmX (1:1000; Sigma), goat anti-MdmX (1:200; Santa Cruz), mouse anti-GSK3β (1:2500; BD transduction) rabbit anti-Cleaved Caspase-3 (1:1000; Cell Signaling), rabbit anti-PARP (1:1000; Cell Signaling), mouse anti-p21 (1:200; Santa Cruz), mouse anti-E2F1 (1:500, Santa Cruz), mouse anti-γH2AX (Ser139) (1:1000; Upstate), rabbit anti-Phospho-Chk2 (Thr68) (1:1000; Cell Signaling), rabbit anti-Hsp90 (1:5000; Calbiochem). Secondary antibodies used in Western blotting were HRP-conjugated, goat anti-rabbit, goat anti-mouse and rabbit anti-goat (1:10,000; Jackson). ECL (Amersham) was used for HRP detection. RNA was extracted from cell pellets in TRI-reagent (Sigma) and isolated using a phenol-chloroform and ethanol precipitation method. cDNA was prepared using MMLV-RT enzyme (Invitrogen). Primers used for CKIα transcript were designed to detect the first two exons of the gene, which are deleted in the knockout, and amplify the exon-exon junction. All other primers were designed for the indicated transcripts, and amplify an exon-exon junction.

Human Cell Lines and RNAi Studies:

RKO and HCT116 cells were cultured in Dulbecco's modified Eagle's medium, supplemented with 10% fetal calf serum (Sigma). DNA damage was induced with Doxorubicin (1 μg/ml) for 6 hours; virion carrying CKIα shRNA and negative control shRNA were generated using lentiviral vectors, transfected into 293T using the calcium phosphate method. Virus was harvested 72 hours post transfection and used to transduce the relevant cell lines. CKIα expression levels were determined before each experiment to ensure adequate knockdown.

Lentiviral Vectors:

Forward and Reverse 64-nt DNA primers corresponding to the CKIα shRNA were ordered from Sigma: Forward primer GATCCCCAAGAAGATGTCCACGCCTGT-TCAAGAGACAGGCGTGGACATCTTCTTTTTTG-GAAA (SEQ ID NO: 1); Reverse Primer: AGCTTTTC-CAAAAAAAGAAGATGTCCACGCCTGTCTCTTGA-ACAGGCGTG-GACATCTTCTTGGG (SEQ ID NO: 2). Primers corresponding to the CKIδ/ε shRNA-Forward primer: GATCCCGGGCTTCTCCTATGACTACT-TCAAGAGAGTAGTCATAGG-AGAAGCCCTTTTTG-GAAA (SEQ ID NO: 3): Reverse primer: AGCTTTTC-CAAAAAGGGCTT-CTCCTATGACTACTCTCTTGA-AGTAGTCATAGGAGAAGCCCGGG (SEQ ID NO: 4). The primer pairs were annealed creating a double strand DNA insert containing 5' BglII and 3' HindIII sites. The annealed shRNA was ligated into a pSUPER vector and excised from pSUPER by XhoI and BamH1 and blunted. The RNAi cassette was ligated into a GFP containing lentiviral targeting vector SIN18-pRLL-CPPT.hEF1-EGFP-WPRE (SIN-GFP) that was digested with EcoRV creating the final recombinant lentiviral vector. The shRNA sequence for CKIδ alone: CCGGCCCATCGAAGTGTTGTG-TAAACTCGAGTTTACACAACACTTCGATG-GGTTTTT (SEQ ID NO: 5). The sequence was ordered from Open Biosystems and cloned in pLKO vector.

Senescence Associated β-Galactosidase Assay:

Fresh intestinal sections were frozen in OCT medium (Sakura Finetek) at −80° C., sliced at 10 μM thickness, fixed for 15 minutes in 0.5% gluteraldehyde in PBS, washed in PBS and PBS pH5.5 containing 1 mM $MgCl_2$. Staining was carried out in the dark at 37° C. for 16 hours in PBS pH5.5, 1 mM $MgCl_2$, 0.2 M potassium ferricyanide, 0.2 M potassium ferrocyanide, 1 μg/ml X-gal. Sections were postfixed in Carnoy's and counterstained with nuclear fast red. Cell cultures were fixed in 2% formaldehyde/0.2% gluteraldehyde in PBS buffer, and stained as above. For immunostaining, cells were post-fixed in 4% paraformaldehyde.

Example 1

Generation of Conditional CKIα, CKIδ and CKIε Knockout Mice

The murine CKIα gene (Csnk1a1) is located on chromosome 18, and includes 10 exons. In order to eliminate kinase activity, and probably ablate the whole protein, the present inventors conditionally deleted the first two exons of the gene, a region that contains the ATP-binding site of the kinase. Therefore, CKIα vector was constructed, harboring a homologous fragment comprised of the targeted exons (1 and 2) and part of the untranslated region of CKIα gene, flanked with two LoxP sites ("foxed"). In addition, the vector includes two homologous fragments of the gene (long and short), and a Neomycin selection marker flanked with a third LoxP site (FIG. 1A). The targeting vector was electroporated into R1 embryonic stem (ES) cells (derived from 129/SVJ mice), and G-418 resistant colonies were picked. DNA was extracted from resistant colonies and used as a template for PCR indicative of a homologous recombination event of the CKIα vector into the ES cell genome.

To obtain colonies that harbor a conditional (floxed) allele it was necessary to excise the Neomycin cassette from the targeted locus, since the presence of a Neomycin gene can interfere with the normal expression of adjacent genes. Therefore, one of the positive clones of ES cells that were isolated was expanded and transiently transfected with a Puromycin resistant plasmid expressing the Cre recombinase protein. Puromycin resistant clones were picked and assayed for a specific loxP recombination event, in which only the Neomycin gene was excised while the first two exons remained intact (FIG. 1B). A single colony in which the desirable event had happened served as a source for establishment of chimeric mice, using the morula aggregation method. The chimeric mice were bred to ICR background mice to readily identify germ-line transmission. The germ-line transmitted progeny carry one wild-type allele and one manipulated allele at their CKIα locus, where two exons of the CKIα gene are flanked by two LoxP sites (floxed allele).

Similarly, CKIδ and CKIε targeting vectors were constructed, in which exon 3 or exons 3 and 4, respectively, containing part of the ATP-binding domain, were floxed, thereby generating mice harboring the targeted alleles.

Example 2

Induction of CKIα Knockout in the Gut

In order to obtain mice in which the CKIα gene is deleted specifically in the intestine, germ-line transmitted progeny were bred to hemizygous Villin-Cre-ER$^{T2}$ mice, which express the Cre recombinase under the transcriptional control of the Villin promoter which is constitutively active in the gut epithelium. The Cre protein is fused to the hormone binding domain of the Estrogen Receptor (ER), which is mutated so that it can only be activated by Tamoxifen—an exogenic analog of estrogen. Systemic administration of Tamoxifen releases the The Cre-ER$^{T2}$ fusion protein from sequestration in the cytoplasm whereby it enters the nucleus and excises the floxed DNA sequence thus creating a null allele only in the gut epithelium (FIG. 1C). Mice were mated to generate progeny that are both homozygous for the floxed CKIα allele and carry the Villin-Cre$^{ER-T2}$ transgene. Control mice were (1) heterozygous floxed CKIα mice harboring Cre-ER$^{T2}$ and (2) homozygous floxed CKIα, lacking the Cre-ER$^{T2}$.

In order to study CKIα deletion in the adult gut, mice were injected with Tamoxifen. No visible phenotype was detected and mice were sacrificed to examine an intestinal phenotype. CKIα loss was detected at the DNA level, by PCR analysis of the deleted sequence (data not shown); at the mRNA level, by RT-PCR analysis (FIG. 2A); and at the protein level, by Western blot analysis (FIG. 2B) and immunohistochemistry (FIG. 2C).

Example 3

Activation of the Wnt/β-catenin Pathway in CKIα Knockout Mice

Figure 3B:
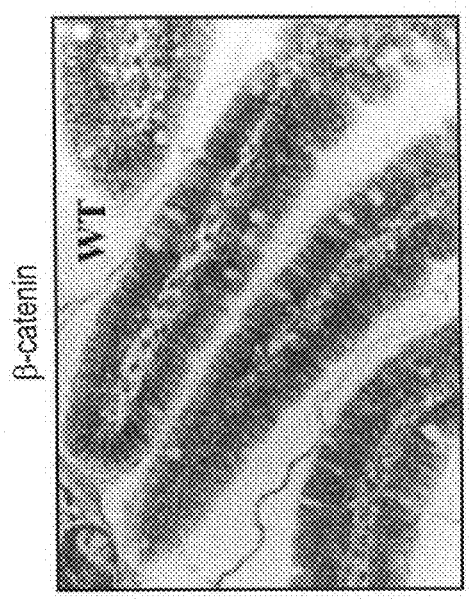
Figure 3C:
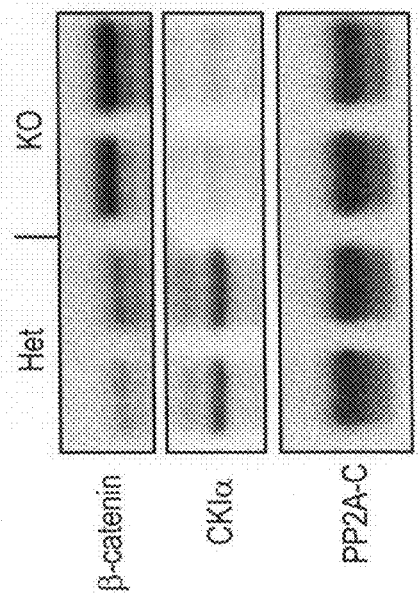
Figure 3D:
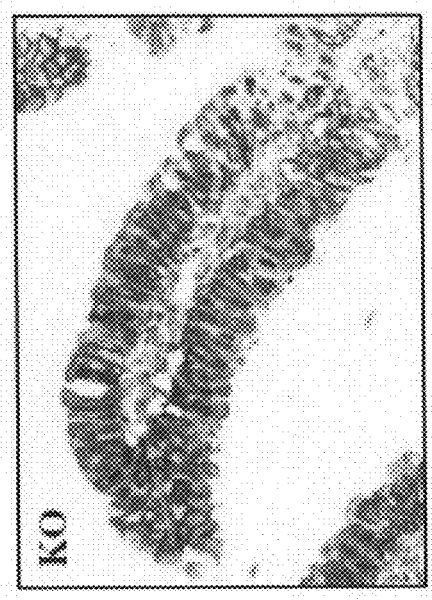

CKIα was shown to negatively regulate the Wnt/β-catenin pathway by priming the phosphorylation-degradation cascade of β-catenin, making it accessible for subsequent GSK3-mediated phosphorylation and βTrCP-mediated ubiquitination. The present inventors therefore stained for β-catenin in the gut and observed an accumulation of β-catenin in the nuclei of mutant villi cells (FIGS. 3A-B). Normally, nuclear β-catenin is only detected in the proliferative compartment which resides in the crypts, as seen in the control gut (not shown). In addition, analysis of phosphorylated Serine-45 of β-catenin in enterocytes showed a reduction in β-catenin phosphorylation at this CKIα-dependent residue (FIG. 3C), which led to stabilization of β-catenin (FIG. 3D).

Figure 4A:
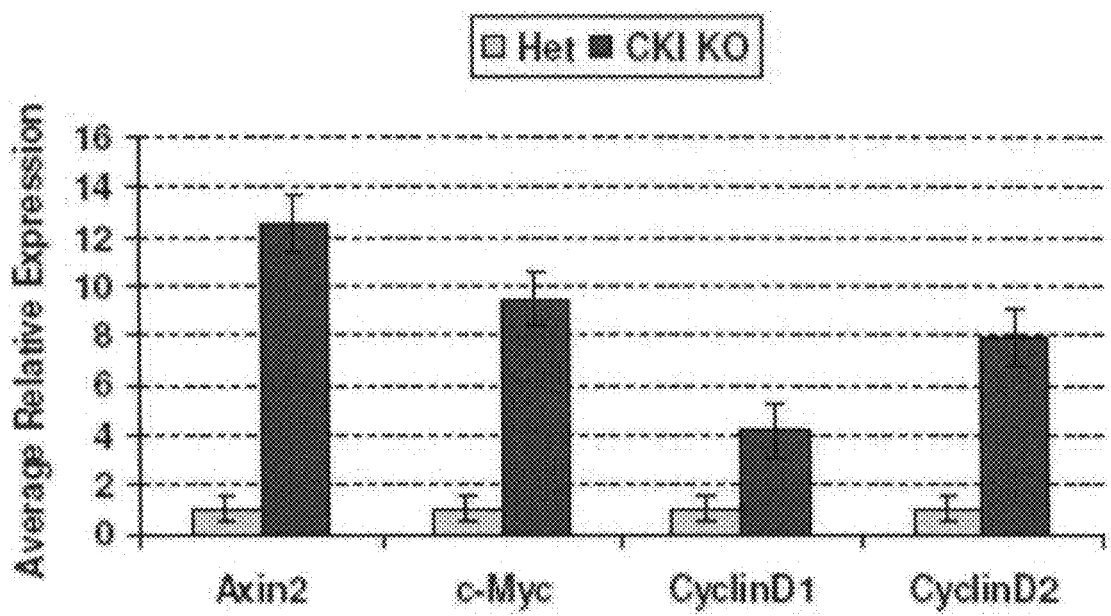
Figure 4B:
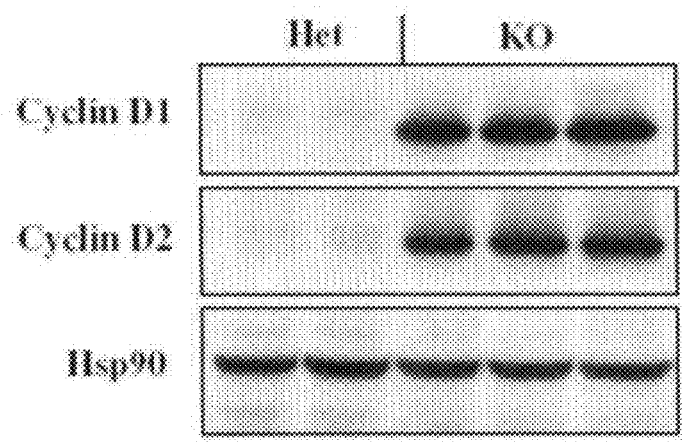
Figure 4C:
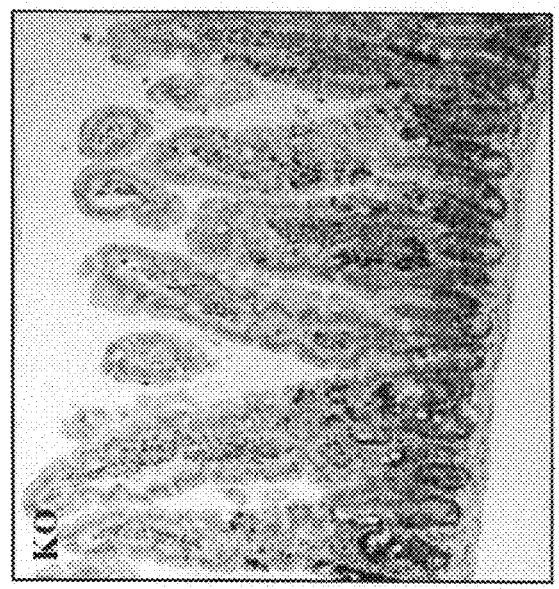
Figure 4D:
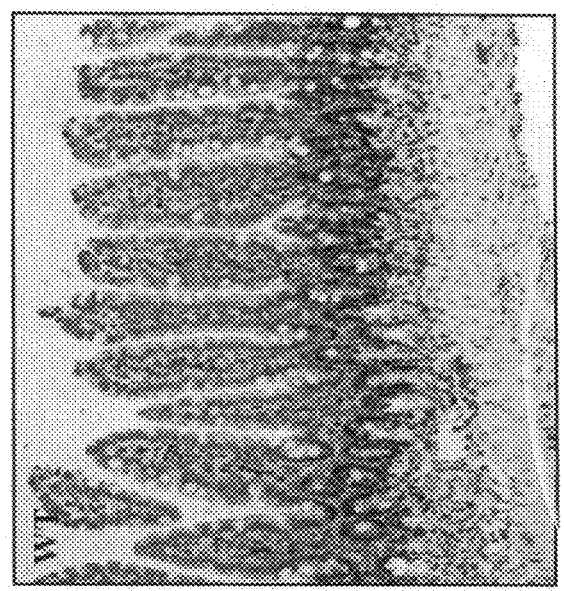

In order to further characterize the Wnt-related phenotype, quantitative RT-PCR was performed to detect a possible up-regulation of Wnt target gene expression. Axin2, c-Myc, Cyclin D1 and Cyclin D2 were all drastically increased in knockout cells compared to control cells (FIG. 4A). Cyclin D1 and D2 up-regulation in knockout cells was also evident in a Western blot analysis (FIG. 4B). Intestinal tissues were also immuno-stained for Cyclin D1 and an increased expression can be observed in the mutant tissue compared to the control tissue (FIGS. 4C-D). While there is a clear evidence for a Wnt phenotype in both the small and large bowel of CKIα-deficient mice, surprisingly, no Wnt-associated tumorigenic lesions (aberrant crypt foci or microadenomas) were evident in the CKIα mutant gut. Hence, it appears that the enhanced proliferation in mutant crypts is curtailed by a mechanism which is evoked by CKIα deficiency, but not by the common Wnt mutations found in cancer (APC, axin and β-catenin).

Example 4

Figure 5A:
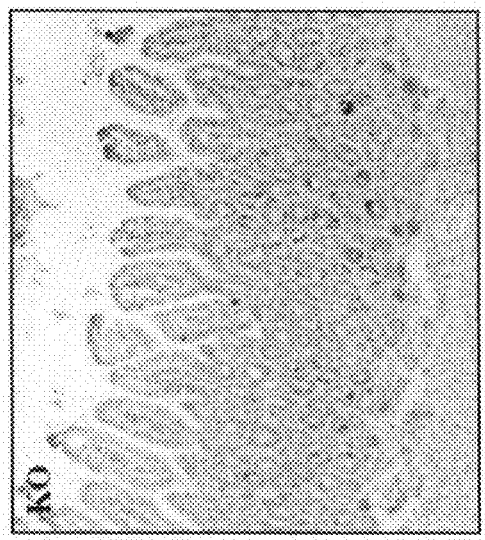
Figure 5B:
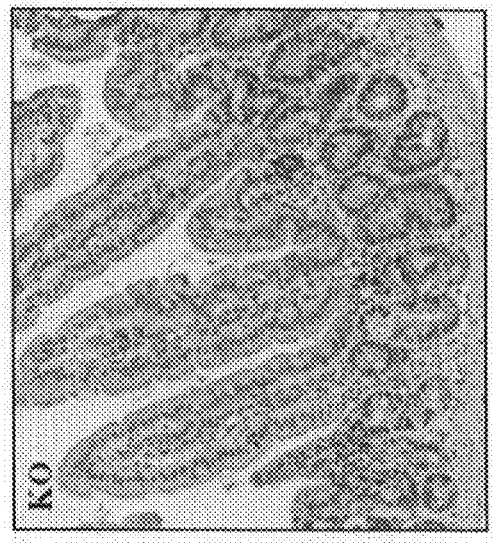
Figure 5C:
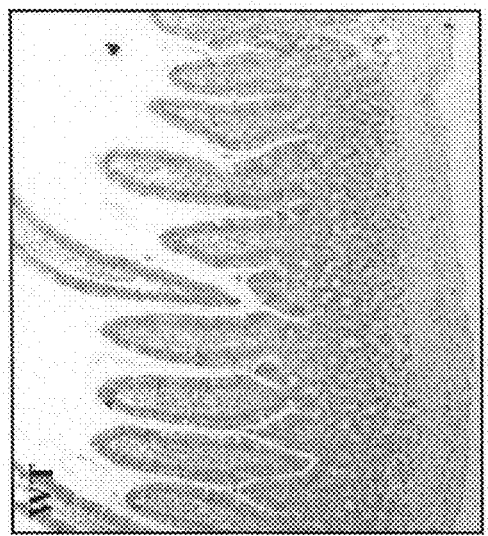
Figure 5D:
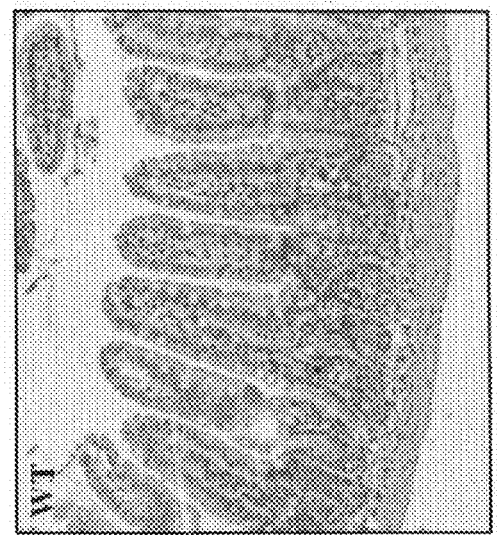
Figure 5E:
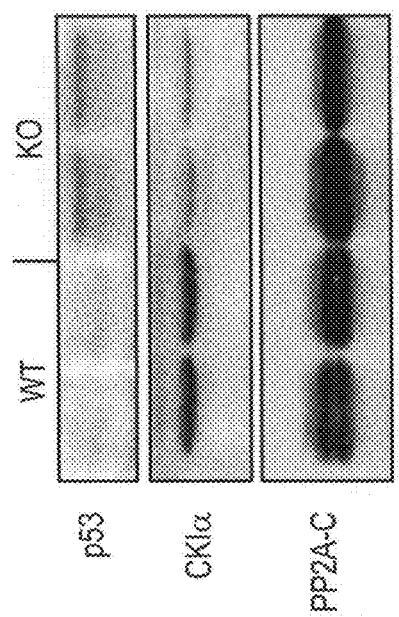
Figure 5F:
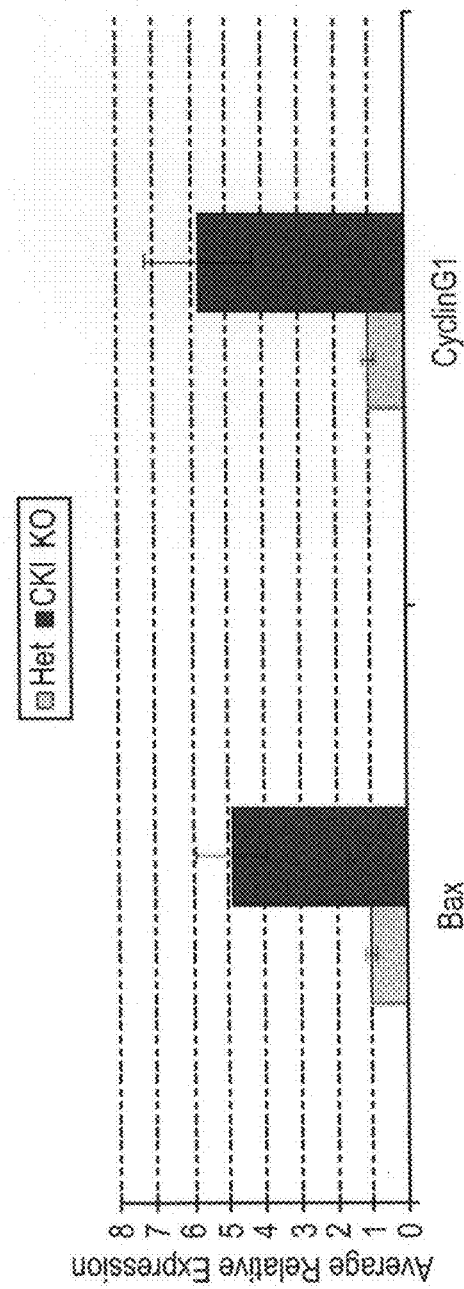
Figure 5H:
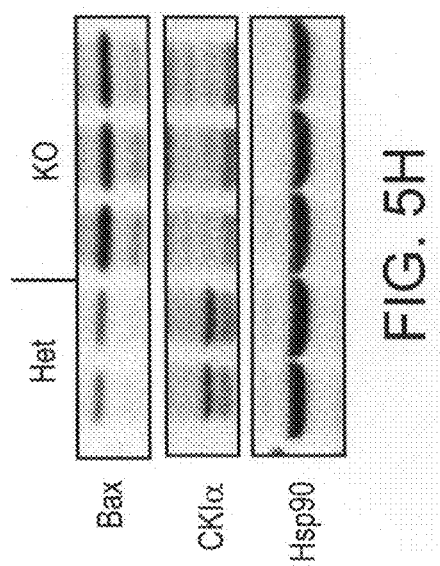
Figure 5G:
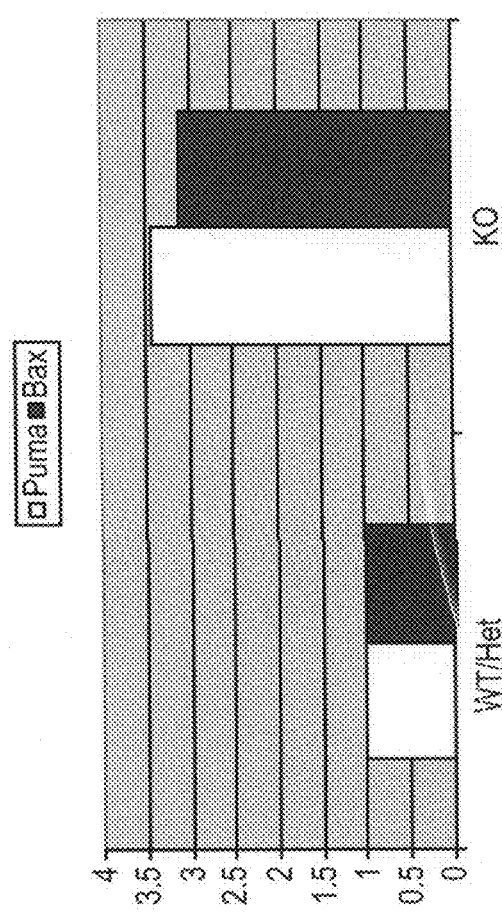
Figure 6C:
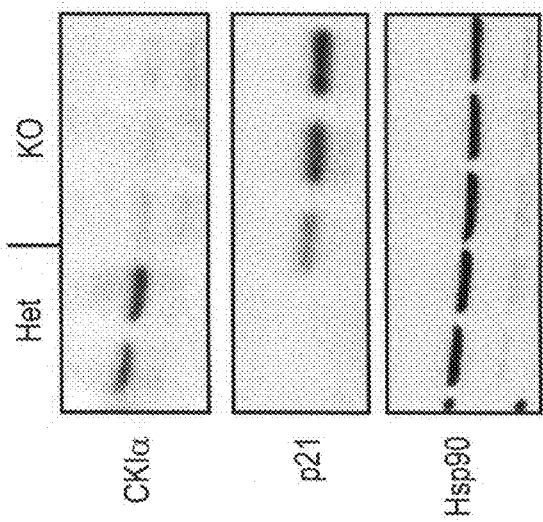
Figure 6A:
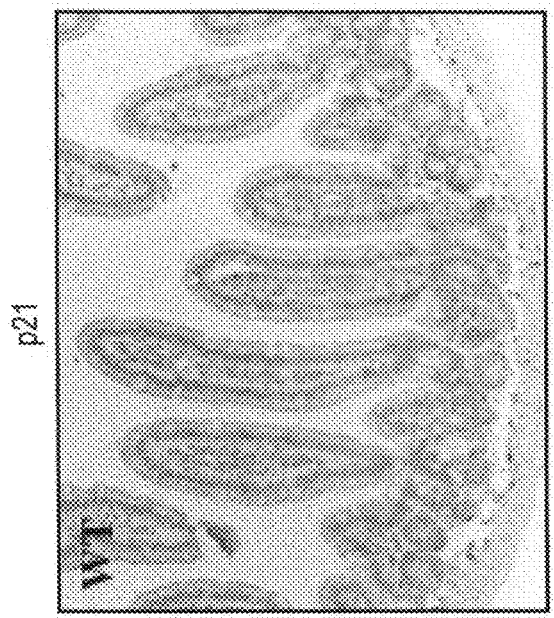
Figure 6B:
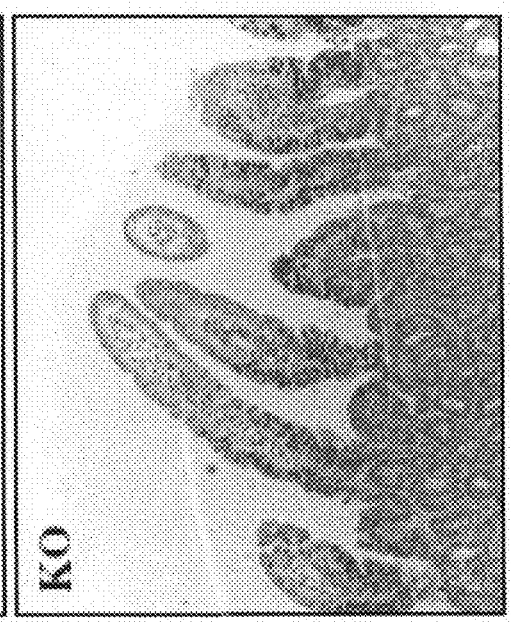
Figures 6D, 6E:
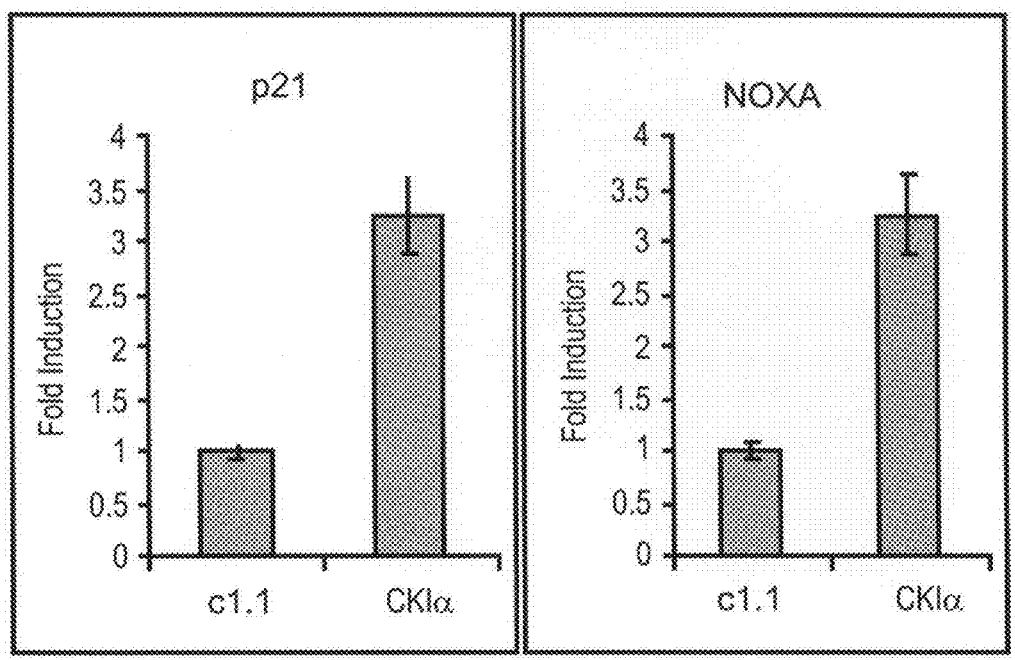
Figures 6F, 6G:
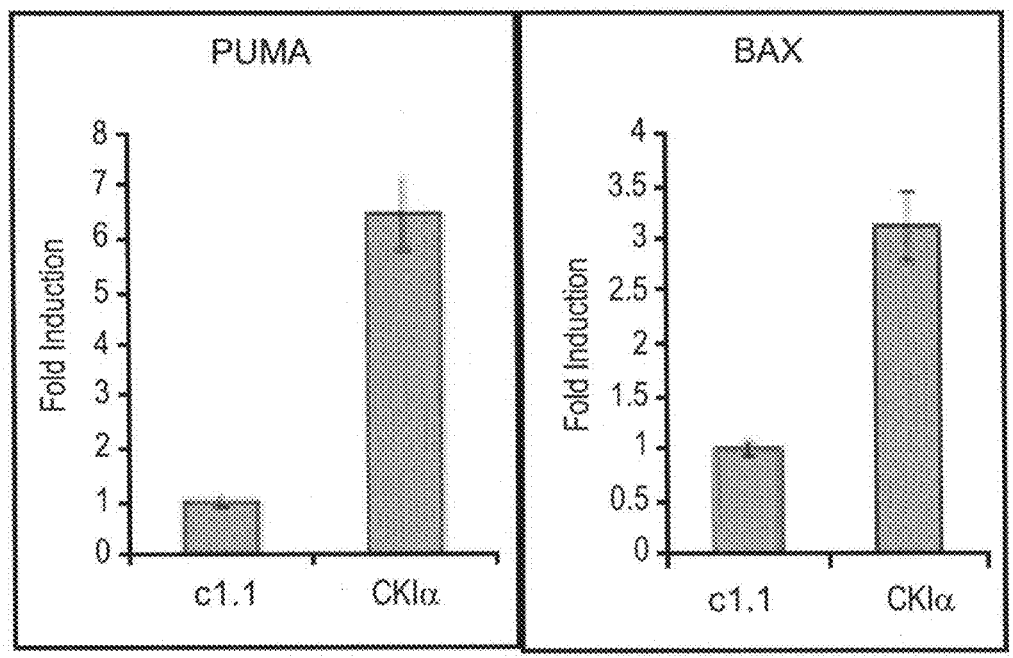

CKIα Ablation Induces a DNA Damage Response in Mouse Gut and Human Colorectal Cancer Cells Resulting in Apoptosis and p53-Mediated Growth Arrest H&E staining of intestinal tissue from the mutant mice showed many apoptotic cells (not shown). To validate this observation, the present inventors stained for activated (cleaved) caspase-3 and confirmed the presence of apoptosis in many crypt cells Compared to mutant mice, control mice showed only physiological apoptosis at the villi tips (FIGS. 5A-B). Whereas apoptosis was limited to intestinal crypts (both small and large bowel), CKIα deletion resulted in p53 activation throughout the crypt-villus axis (FIGS. 5C-E), which induced vigorous expression of the cell growth inhibitor p21 (Waf1/Cip1) (FIGS. 6A-C), explaining the cessation of proliferation at the crypt-villus border. In addition, p53 target genes such as Bax, Puma and Cyclin G1 were upregulated in CKIα KO mice (FIGS. 5F-H). Hence, it appears that upon CKIα ablation, excessive Wnt-induced proliferation in the crypts is balanced by apoptosis and p53/p21-mediated growth arrest. Supporting this conclusion is the induction of pro-apoptotic genes and p21 upon CKIα knock-down (KD) in RKO colon carcinoma cells (FIGS. 6D-G)

The tumor suppressor p53 is negatively controlled by proteasomal degradation, mediated through the E3-ubiquitin ligase Mdm2. Another level of regulation on p53 is carried out by MdmX, which inhibits p53's trans-activation function, without affecting its protein levels. MdmX analysis on a Western blot indicated that while in control cells MdmX is stably expressed, in CKIα mutant cells there is remarkable reduction in MdmX protein levels. This decrease was in direct correlation with the reduction in CKIα expression (FIG. 7A). To exclude a transcriptional downregulation effect of CKIα on the MdmX gene, RT-PCR was performed. Contrary to the reduction in protein level the MdmX transcript was slightly up-regulated, possibly representing a feedback process (FIG. 7B). Since MdmX is known to be degraded in response to DNA damage, it may be hypothesized that CKIα loss could induce a DNA damage response (DDR). Indeed, immunostaining for a DDR marker, phospho-Histone H2A.X (γH2A.X) demonstrated extensive DDR throughout CKIα-deficient crypts (FIGS. 8A-B). Furthermore, siRNA-mediated CKIα depletion in human colorectal carcinoma cell lines resulted in H2A.X phosphorylation, HdmX (human homolog of mdmX) loss, p53 stabilization and apoptosis, recapitulating the CKIα knockout phenotype in mice (FIGS. 8C-E). These observations are supported by similar results in melanoma cells (FIG. 8F).

Example 5 p53 Activation Restrains the Proliferative Effects of Wnt in CKIα Knockout Mice

Figure 9D:
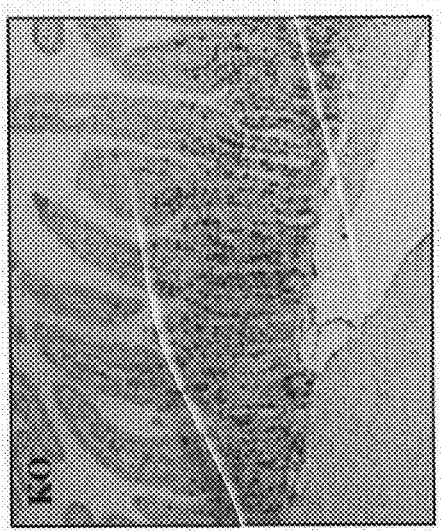
Figure 9H:
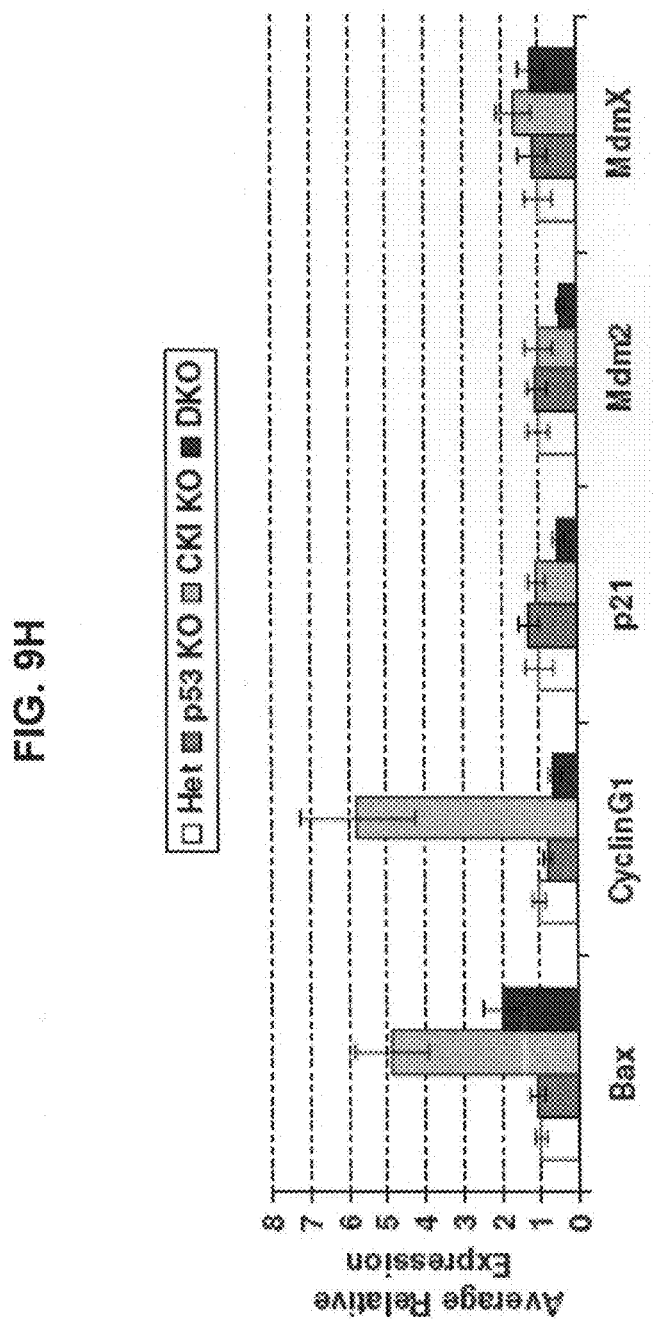

To assess the contribution of p53 activation to the novel homeostasis observed in CKIα knockout gut, conditional CKIα knockout mice were crossed onto conditional p53 knockout mice and a double deletion was generated in the gut epithelium via tamoxifen-induced Vil-Cre (p53-deficient mice, as well as gut-specific p53-conditional knockout mice show normal gut functions and histology, at least up to 6 months in age). In contrast, double CKIα/p53 mutants developed severe multi-focal intra-mucosal carcinomas throughout the gut epithelium in a short period of 2 weeks (FIG. 9A-B). Carcinoma foci were characterized by extensive proliferation spread into the villi compartment, as evidenced by extensive BrdU and Ki67 staining (FIGS. 9C-D and data not shown). Wnt target genes, such as Axin2, c-Myc, CyclinD1 and CyclinD2 were upregulated in the double CKIα/p53 mutants similarly to the observed in single CKIα mutants (FIG. 9E); but unlike in the single CKIα mutants, Cyclin D1 staining in double mutants was extended into the villi, particularly into carcinoma foci (FIGS. 9F-G). The p53 target genes Bax and Cyclin G1, which were induced in the single CKIα knockout mice, remained almost at basal levels in the double knockout mice, whereas other p53 targets such as p21 and Mdm2, which were not induced in CKIα knockout mice at the mRNA levels, were drastically reduced in the double knockout mice (FIG. 9H). Remarkably, side by side with the enhanced proliferation, double CKIα/p53 mutant gut exhibited extensive crypt apoptosis as seen by histological examination and cleaved caspase-3 immunostaining, similar to the CKIα-deficient wild-type-p53 gut (FIGS. 10A-B). On the other hand, p21 expression which was highly induced in single CKIα mutant mice was completely abolished in the double mutants (FIGS. 10C-D), indicating that the growth arrest function of p53 rather than its pro-apoptotic role is the barrier against Wnt-driven abnormal proliferation and tumorigenesis in the gut. $p21^{(Cip1/Waf1)}$ expression is regulated in a p53-dependent and p53-independent manner and its total absence at the protein level and severe mRNA reduction in double KO mice indicated that it is likely eliminated by several mechanisms. The E2F1 signaling pathway may account for both the p53-independent apoptosis and p21 abolishment since, although E2F family members are positive regulators of cell cycle progression, they also contribute to apoptosis in a context-dependent manner, particularly in proliferating cells. The present inventors detected a significant induction of the E2F1 protein (FIG. 11A) and its target genes, p73 and Cyclin E1, in CKIα mutants and even stronger in double CKIα/p53 mutants (FIG. 11B). The E2F1 pathway has recently been shown to control p21 expression through specific microRNAs, and indeed, CKIα-deficient enterocytes and particularly double p53-CKIα mutant enterocytes had enhanced mRNA levels of the microRNA host gene Mcm7, compared to WT and p53-deficient cells (FIG. 11B). Hence, p21 which appears as the key barrier against abnormal Wnt-proliferation in the gut is likely being compromised in the double mutant mice by both the absence of p53 and the induction of the E2F1 pathway. Conceivably, in the absence of p21 in double mutant mice, E2F1-induced apoptosis is particularly effective, possibly explaining the similar levels of apoptosis in single and double mutant crypts.

Example 6

CKIα Ablation Provokes Cell Senescence which Induces Inflammation in a Cell Non-Autonomous Manner The transcription profile of CKIα-deleted intestine reveals an atypical inflammatory response not found in APC mutant mice, including the upregulation of several inflammation-associated genes, among them TNFα and the TNF-R family member TROY; Toll-like receptors (TLR) 1 and 2; and IL1-R antagonist (FIGS. 12A-B). Specifically, these genes are putative transcriptional targets of NF-κB, so the present inventors tested for nuclear localization of the p65 subunit of NF-κB, finding p65-NF-κB positive nuclei in the villi of CKIα-deleted mice but not control heterozygotes, which may account for the induction of this inflammatory program (FIGS. 12C-D).

Figure 13A:
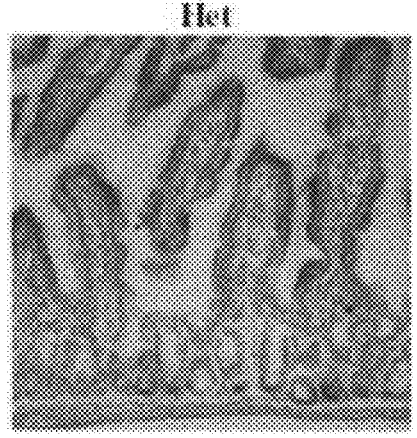
Figure 13B:
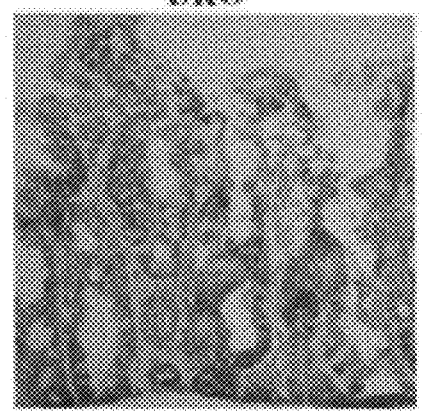
Figure 13C:
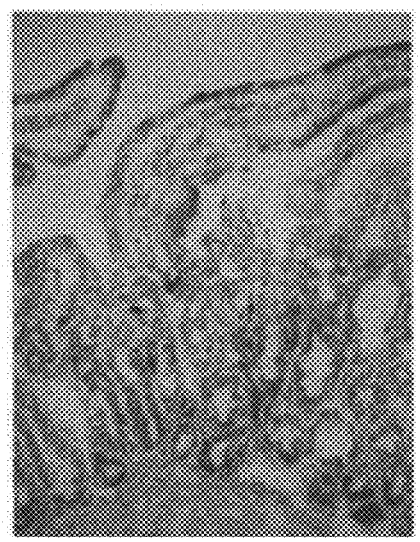
Figure 13D:
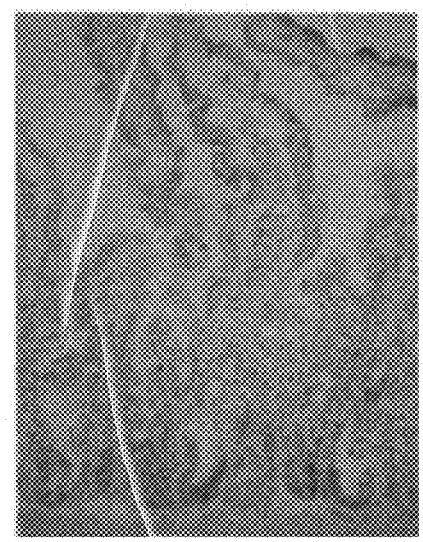
Figure 14A:
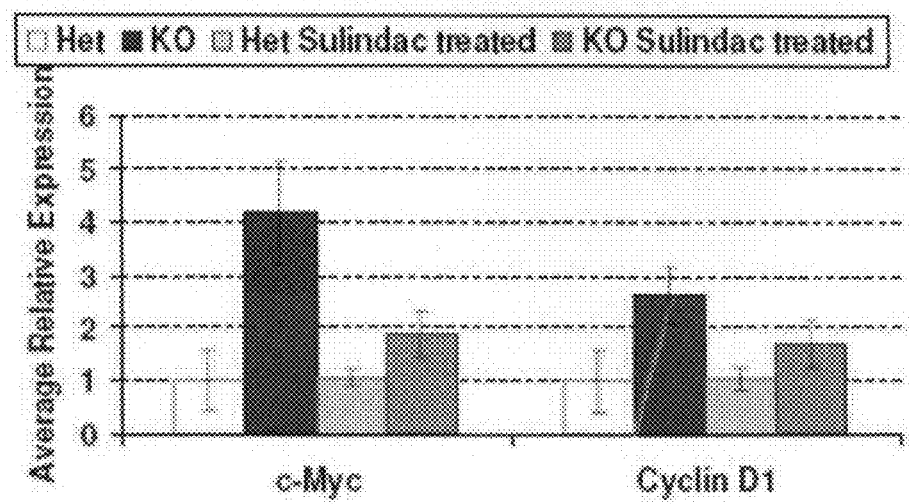
Figure 14B:
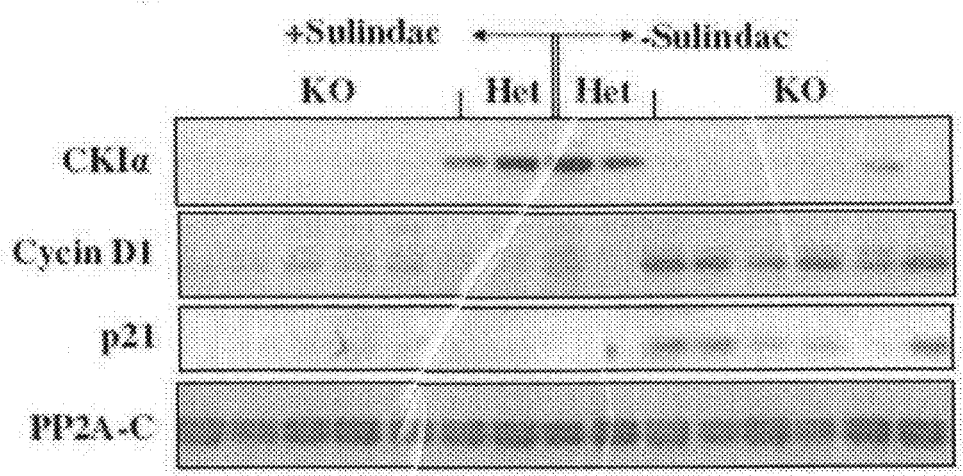
Figure 14C:
Figure 14F:
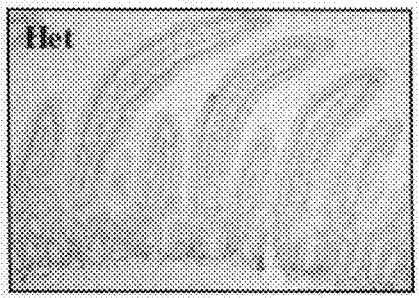
Figure 14D:
Figure 14G:
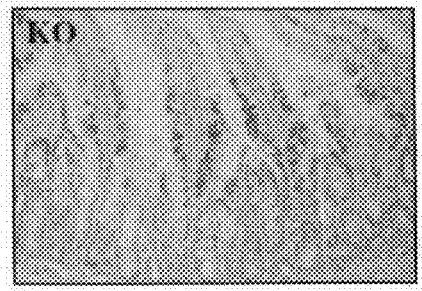
Figure 14E:
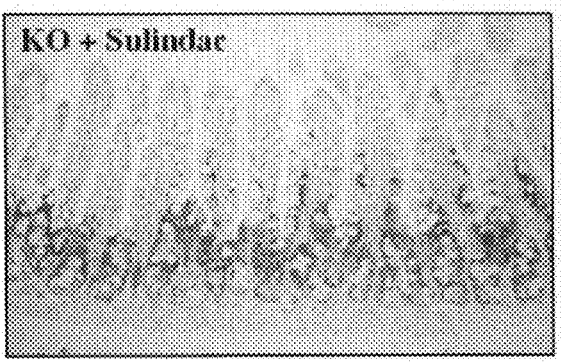
Figure 14H:
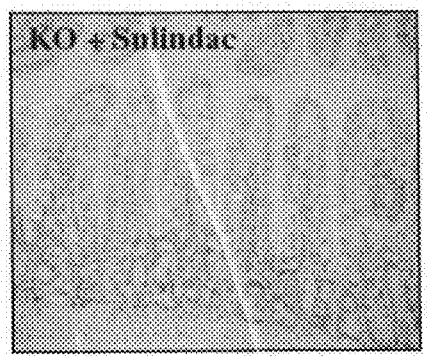
Figure 14I:
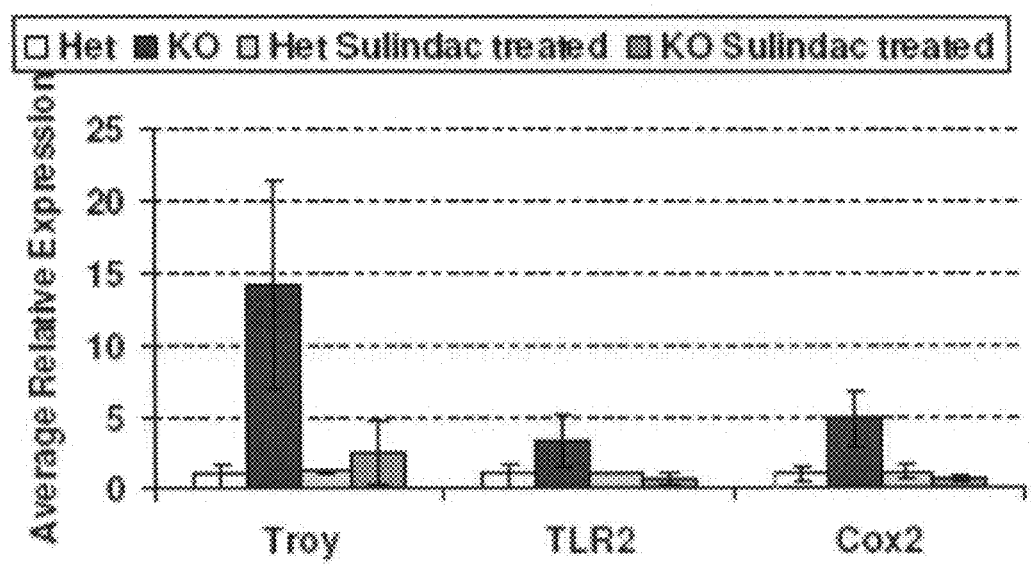

A potential source of inflammation was identified through the detection of cell senescence in the gut of CKIα-deleted mice. In a senescence associated β-galactosidase assay (SA-β-gal), strongly positive cells were found in CKIα KO mice, with a distinct perinuclear stain, but not in heterozygous mice. Apparently, this senescence is p53-independent, as numerous β-gal-positive cells were also observed in CKIα/p53 DKO (FIGS. 13A-C).

Senescence in cell culture and human cancer is thought to be mediated by a non-cell autonomous inflammatory signaling cascade, therefore the present inventors tested whether the phenotype of CKIα mutant gut depends on such a mechanism. To inhibit the inflammatory process CKIα knockout mice were fed with the NSAID Sulindac for the duration of the experiment. A significant reduction was found in nearly all markers for Wnt activation, inflammation, senescence and cell growth arrest, including CyclinD1, Troy, Cox2, SA-β-gal and p21 (FIGS. 13C-D, FIGS. 14A-I), and the overall phenotype of the gut tissue was greatly reduced in the severity of dysplasia. Surprisingly, many clusters of cells were found with high grade dysplasia in the villi of sulindac fed CKIα KO mice, which are never found in control mutant mice, indicating an anti-carcinogenic role for inflammation. It may therefore by concluded that the non-cell autonomous inflammatory process in CKIα KO mice is necessary for upregulation of pro-tumorigenic Wnt genes, as well as for the counter response including p21 induction, and that senescence in these mice is tightly connected to this inflammatory response.

Example 7

Loss of CKIα Causes Growth Arrest and Senescence in Human Cell Lines and Colorectal Tumors The established method for measuring cell senescence is in cell culture. Accordingly, the IMR90 human cell line was tested for senescence upon CKIα knockdown. It was found that IMR90 cells were positive for SA-β-gal and have senescence associated nuclear foci of γH2A.X twelve days following lentiviral transduction with a CKIα shRNA expression vector (FIGS. 15A-F), indicating a direct role for CKIα loss in the initiation of cellular senescence. When the CKIα protein levels were examined in human colorectal polyps, it was found that nearly all samples showed heterogeneous staining for CKIα, while in normal mucosa CKIα levels were even throughout the epithelium. The inventors further tested whether reduction in CKIα levels is associated with senescence and cell growth arrest by staining for the proliferation marker, Ki67, the senescence marker, IL-8 and the mediator of cell growth arrest, p21. In most polyps there was a general correlation between IL-8 upregulation in the epithelial cytoplasm and a distinct reduction in CKIα, as well as reduced Ki67 (FIGS. 15G-J). In a few tumors highly correlative patches of cells were found showing coinciding patterns of mutually exclusive expression between CKIα and Ki67 on the one hand and p21 and IL-8 on the other, indicating that CKIα levels may be dynamically regulating cell cycle exit, growth arrest and senescence in human colorectal cancer (FIGS. 15G-J).

Example 8

APC Mutation Augments the CKIα Mutant Phenotype

The multiple intestinal neoplasias (min) mouse has a single truncated APC allele ($APC^{+/min}$) and is a model for the human FAP hereditary colorectal cancer syndrome. In both min and FAP, loss of the normal, full length APC allele in the intestinal epithelium results in adenomas (in mice this is mainly in the small intestine). While hemizygocity at the mutant APC locus results in deregulation of the Wnt/β-catenin pathway, with excessive proliferation and tumorigenesis, heterozygous expression of both wild-type and truncated APC protein is compatible with normal life span, differentiation and function of the epithelial cells. To assess the relationship between CKIα deficiency and the APC mutation with respect to the Wnt phenotype, cell cycle checkpoint control and the development of cancer, the conditional CKIα knockout mice was crossed with the APC$^{+/min}$ mice.

Figure 16A:
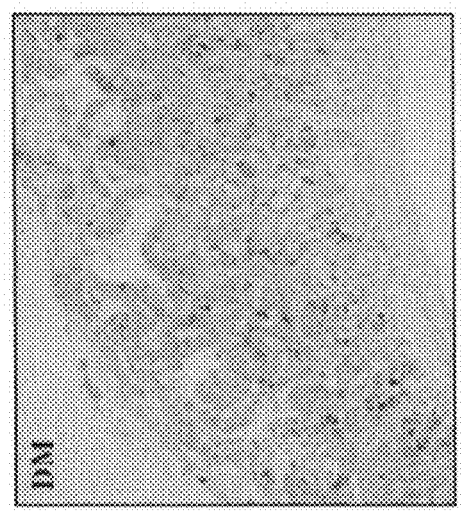
Figure 16B:
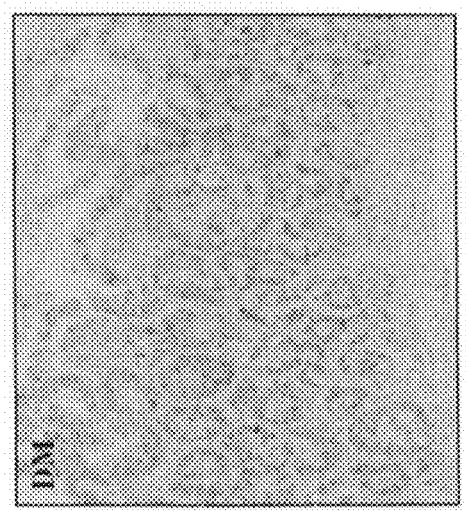
Figure 16C:
Figure 16D:
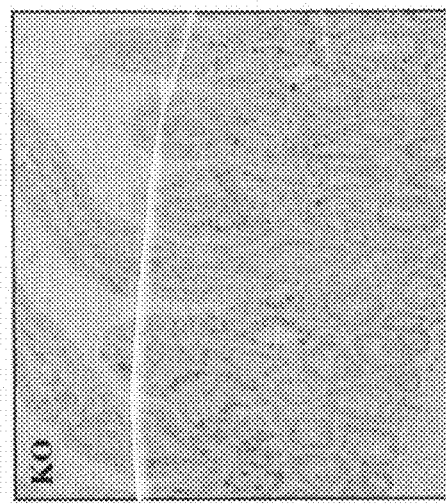
Figure 16E:
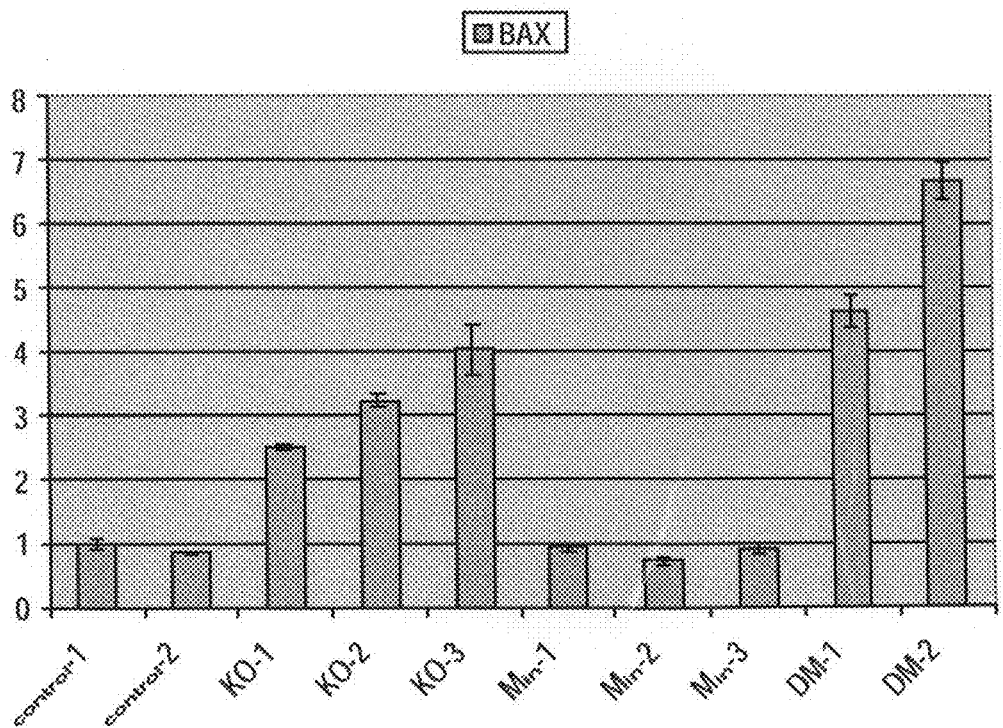
Figure 16F:
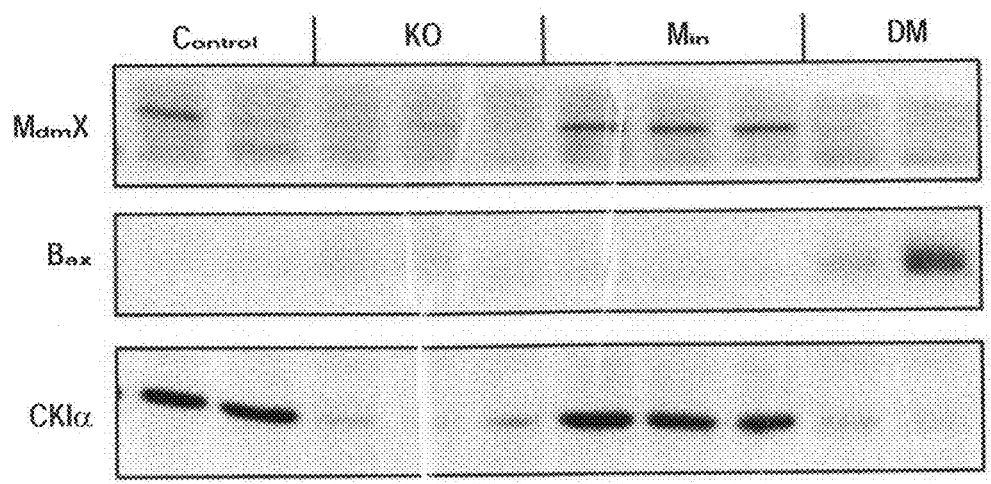
Figure 18A:
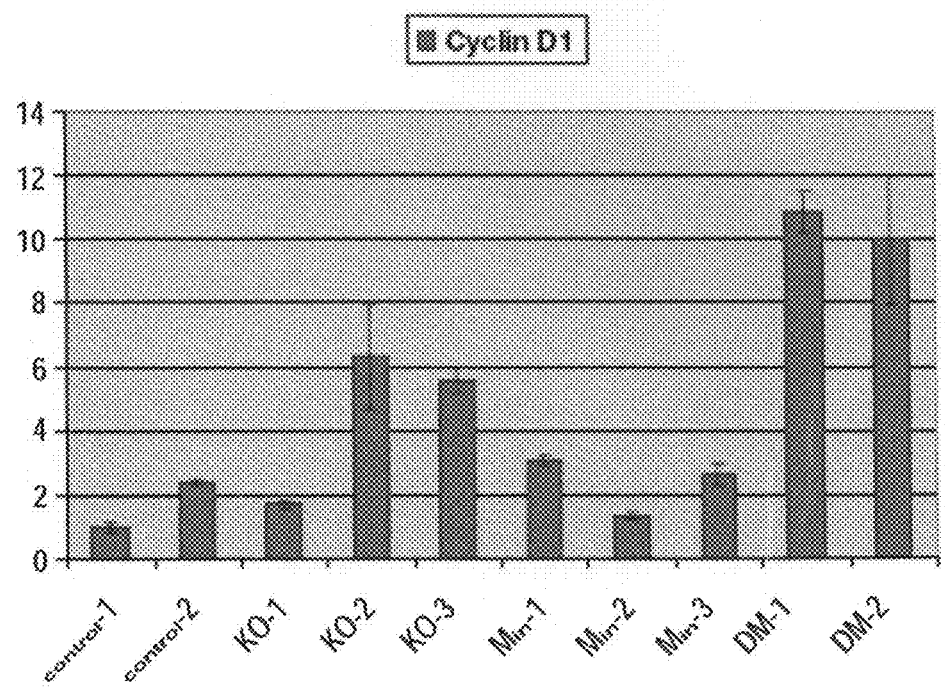
Figure 18B:
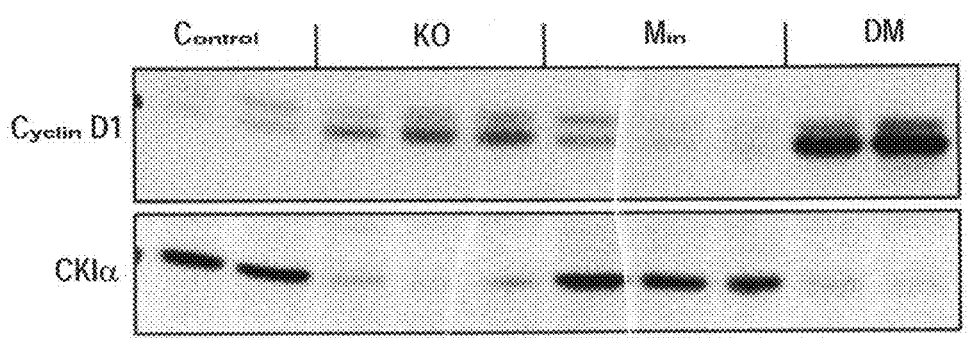

On a mixed 129/ICR/C57BL/6 background, at the age of 2 months, the double mutant mice (conditional CKIα knockout and APC$^{+/min}$) developed microadenomas similarly to APC$^{+/min}$ mice on the same genetic background. When intestinal tissues were stained for activated caspase-3 to detect the level of apoptosis, it was evident that compared to a non-destructive apoptosis observed in the CKIα knockout mice, double mutant mice had widespread intestinal apoptosis, which ruined the tissue architecture (FIGS. 16A-B). Indeed, mediators of apoptosis such as Bax are greatly elevated in CKIα knockout/APC$^{+/min}$ double mutant mice (DM) compared to CKIα knockout (KO) or APC$^{+/min}$ alone (FIGS. 16E-F). In addition, the double mutant mice induce p53 all over the gut epithelium to a level that is far beyond the p53 induction seen in CKIα knockout mice (FIGS. 16C-D). The increased p53 response in double mutants is unlikely to be due to loss of MdmX, since MdmX is already very low in single CKIα KO (FIG. 16F). It is likely that additional, MdmX-independent mechanisms account for the augmented p53 response in double mutant enterocytes, beyond that of CKIα-mutant cells alone.

BrdU staining of the CKIα knockout/APC$^{+/min}$ double mutant gut showed enhanced proliferation, extending to the villi compartment, compared to a slight increase in proliferation in the CKIα knockout, which was limited to the crypts (FIGS. 17A-C). Cyclin D1 staining and Western blot analyses showed synergistic upregulation of Cyclin D1 expression in the double mutant, compared with CKIα knockout mice. This was also confirmed at the RNA level by RT-PCR (FIGS. 18A-D). It is likely that ectopic proliferation in the villi is a response to the widespread apoptosis.

Figure 19A:
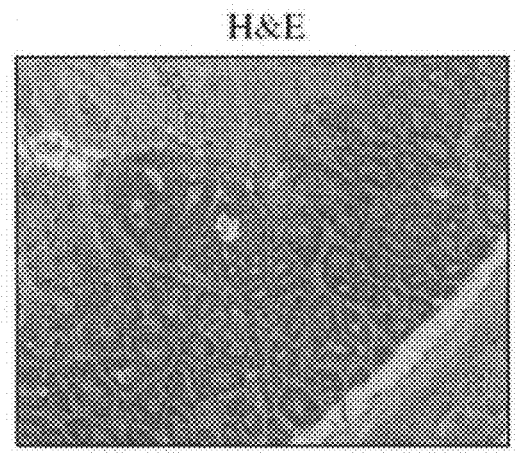
Figure 19B:
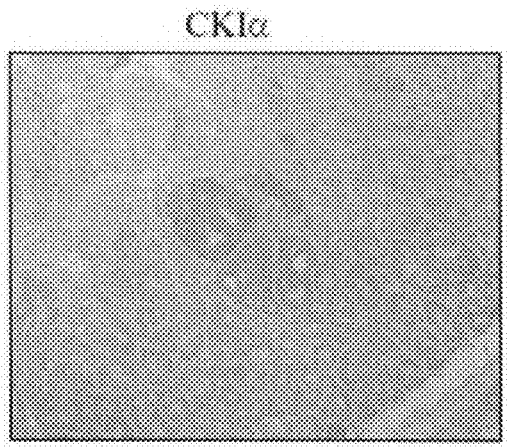
Figure 19C:
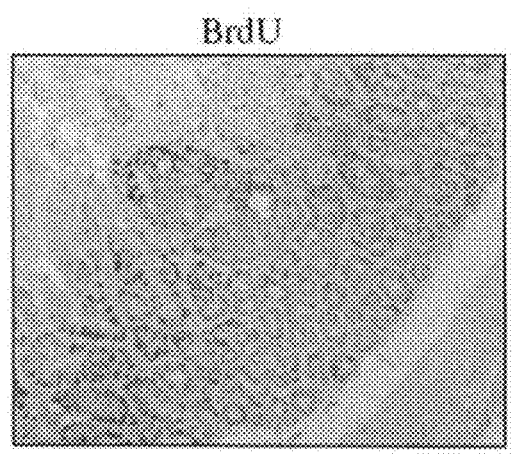
Figure 19D:
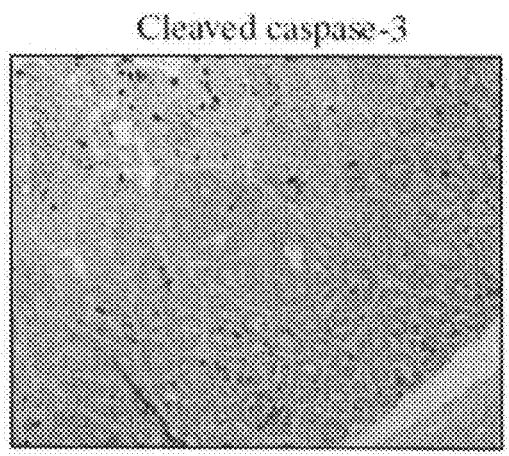
Figure 19E:
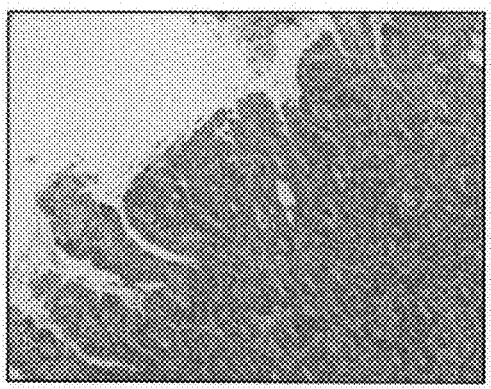
Figure 19F:
Figure 19G:
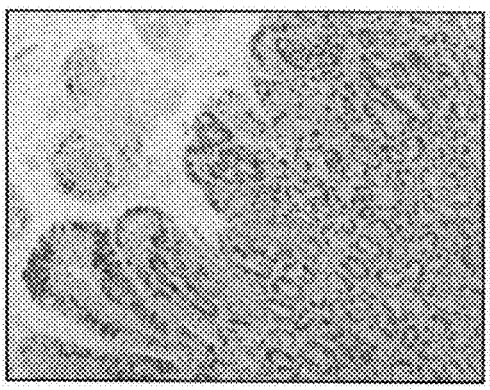
Figures 20A, 20B, 20C, 20D, 20E, 20F:
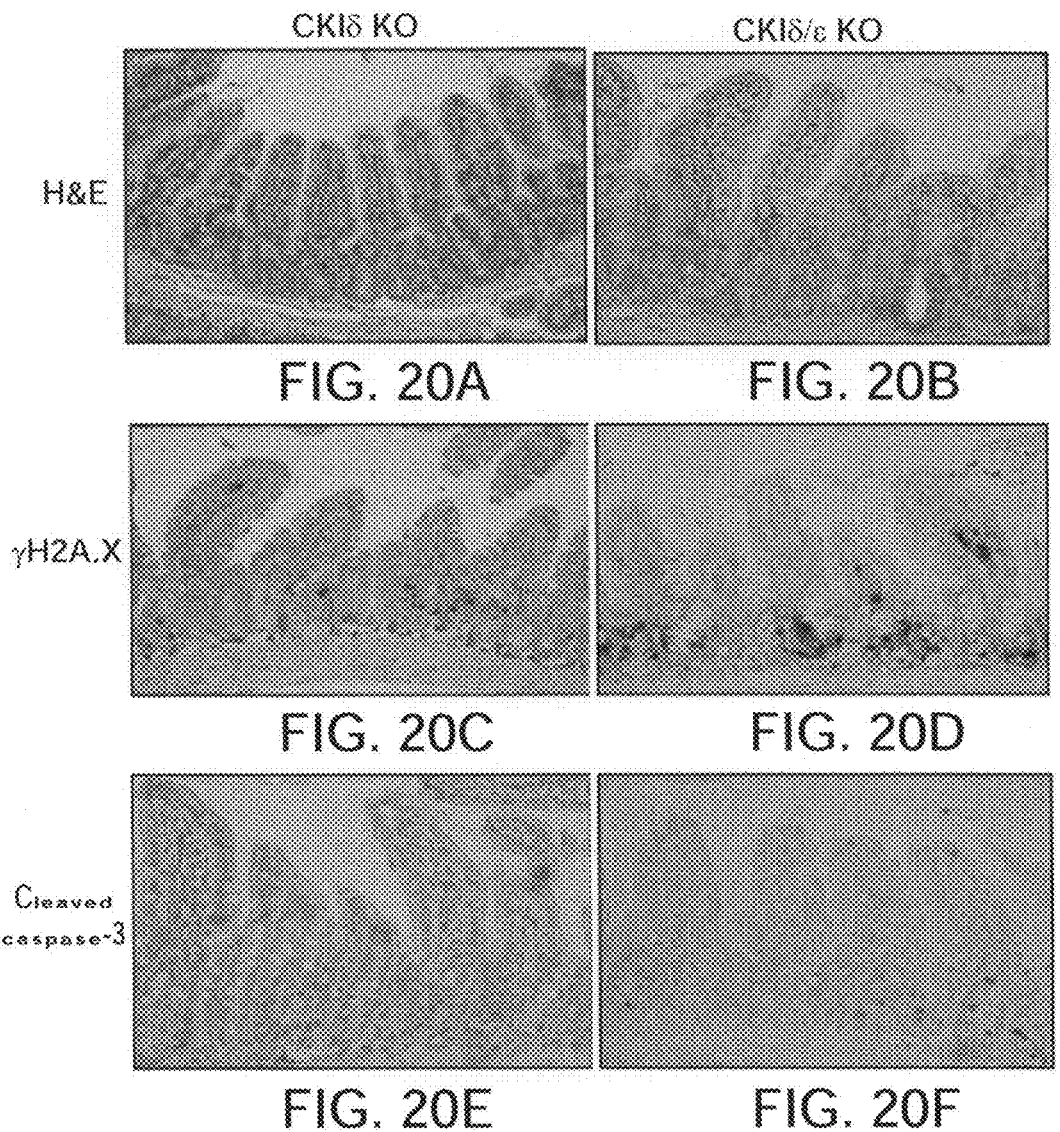
Figure 20H:
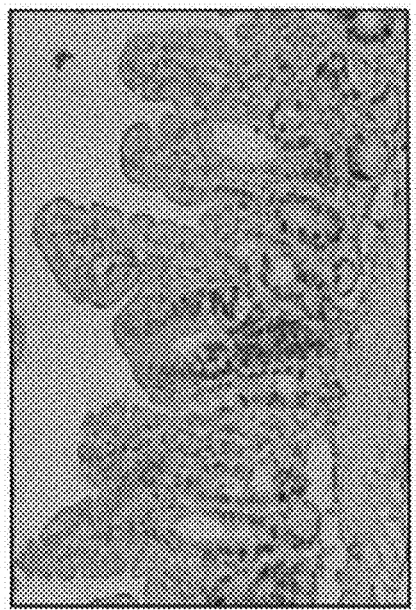
Figure 20J:
Figure 20G:
Figure 20I:

If CKIα deficiency sensitizes APC$^{+/min}$ cells to apoptosis and p53-mediated cell growth arrest, then adenoma formation should be reduced in double mutants. Whereas at 2 months of age, a significant reduction of the microadenoma frequency in double mutants mice could not be observed (macroadenomas are usually non-apparent at that early age in APC$^{+/min}$ mice of that genetic background), it was noticed that all microadenomas and aberrant crypt foci were CKIα positive (see examples in FIGS. 19A-B and 19E-F). Furthermore, while apoptosis was evident in the CKIα-negative tissue surrounding the double mutant microadenoma, the adenoma itself, which is CKIα-positive, was devoid of apoptotic cells (FIG. 19D). These preexisting adenomas in the double mutants retain CKIα levels due to inefficient expression of Villin-Cre within the adenoma (data not shown). However, all of the newly-derived microadenomas that developed during the CKIα ablation period were also CKIα-positive and likely originated from CKIα-deletion-spared stem cells. It may therefore be concluded that de novo APC$^{+/min}$ microadenomas do not tend to appear on a CKIα-negative background and suggest a synthetic lethality between CKIα deletion and APC$^{+/min}$ mutation.

Example 9

Loss of CKIδ and CKIε in Mice Results in a DNA Damage Response, Apoptosis and Cell Cycle Arrest CKIε knockout mice develop normally, with no visible phenotypes either in the gut or elsewhere, whereas CKIδ knockout mice die at birth. Therefore CKIδ was specifically ablated in the mouse gut using the vil-Cre-ER$^{T2}$ driver. These mice showed signs of DNA damage response, demonstrated by γH2A.X staining, accompanied by crypt cells apoptosis (FIGS. 20A-F); moreover, p53 was induced in these crypts, accompanied by p21 upregulation (FIGS. 20G-J). Interestingly, intestinal deletion of CKIδ in CKIε KO mice augmented the DDR-p53-p21 phenotype, and CKIδ/CKIε double knockout gut show severe DDR, profound apoptosis, and robust p53/p21 induction in the crypt compartment (FIGS. 20A-J). Furthermore, in contrast to CKIα KO, deletion of delta and epsilon has no activating effect on the Wnt pathway. The lack of Wnt activation combined with p53/p21 growth arrest likely explains the extensive crypt loss we observe in the CKIδ/CKIε double knockout mice (FIGS. 20A-B). siRNA-mediated mRNA depletion of both CKIδ and CKIε resulted in a pronounced DNA damage response (H2A.X phosphorylation) in a human colorectal carcinoma cell line and CKIδ depletion induced p53 stabilization, recapitulating the CKIδ/CKIε KO phenotype in mice (FIG. 21).

REFERENCES

1. Cadigan, K. M. & Nusse, R. Wnt signaling: a common theme in animal development. *Genes Dev* 11, 3286-305 (1997).
2. Peifer, M. & Polakis, P. Wnt signaling in oncogenesis and embryogenesis—a look outside the nucleus. *Science* 287, 1606-9 (2000).
3. Wodarz, A. & Nusse, R. Mechanisms of Wnt signaling in development. *Annu Rev Cell Dev Biol* 14, 59-88 (1998).
4. Willert, K. & Nusse, R. Beta-catenin: a key mediator of Wnt signaling. *Curr Opin Genet Dev* 8, 95-102 (1998).
5. Cliffe, A., Hamada, F. & Bienz, M. A role of Dishevelled in relocating Axin to the plasma membrane during wingless signaling. *Curr Biol* 13, 960-6 (2003).
6. Wang, J. & Wynshaw-Boris, A. The canonical Wnt pathway in early mammalian embryogenesis and stem cell maintenance/differentiation. *Curr Opin Genet Dev* 14, 533-9 (2004).
7. Maretto, S. et al. Mapping Wnt/beta-catenin signaling during mouse development and in colorectal tumors. *Proc Natl Acad Sci USA* 100, 3299-304 (2003).
8. Bienz, M. & Clevers, H. Linking colorectal cancer to Wnt signaling. *Cell* 103, 311-20 (2000).
9. Polakis, P. Wnt signaling and cancer. *Genes Dev* 14, 1837-51 (2000).
10. Amit, S. et al. Axin-mediated CKI phosphorylation of beta-catenin at Ser 45: a molecular switch for the Wnt pathway. *Genes Dev* 16, 1066-76 (2002).
11. Liu, C. et al. Control of beta-catenin phosphorylation/degradation by a dual-kinase mechanism. *Cell* 108, 837-47 (2002).
12. Yanagawa, S. et al. Casein kinase I phosphorylates the Armadillo protein and induces its degradation in *Drosophila*. *Embo J* 21, 1733-42 (2002).
13. McKay, R. M., Peters, J. M. & Graff, J. M. The casein kinase I family: roles in morphogenesis. *Dev Biol* 235, 378-87 (2001).
14. McKay, R. M., Peters, J. M. & Graff, J. M. The casein kinase I family in Wnt signaling. *Dev Biol* 235, 388-96 (2001).
15. Peters, J. M., McKay, R. M., McKay, J. P. & Graff, J. M. Casein kinase I transduces Wnt signals. *Nature* 401, 345-50 (1999).

16. Sakanaka, C., Leong, P., Xu, L., Harrison, S. D. & Williams, L. T. Casein kinase iepsilon in the wnt pathway: regulation of beta-catenin function. *Proc Natl Acad Sci USA* 96, 12548-52 (1999).
17. Gao, Z. H., Seeling, J. M., Hill, V., Yochum, A. & Virshup, D. M. Casein kinase I phosphorylates and destabilizes the beta-catenin degradation complex. *Proc Natl Acad Sci USA* 99, 1182-7 (2002).
18. Fish, K. J., Cegielska, A., Getman, M. E., Landes, G. M. & Virshup, D. M. Isolation and characterization of human casein kinase I epsilon (CKI), a novel member of the CKI gene family. *J Biol Chem* 270, 14875-83 (1995).
19. Graves, P. R., Haas, D. W., Hagedorn, C. H., DePaoli-Roach, A. A. & Roach, P. J. Molecular cloning, expression, and characterization of a 49-kilodalton casein kinase I isoform from rat testis. *J Biol Chem* 268, 6394-401 (1993).
20. Rowles, J., Slaughter, C., Moomaw, C., Hsu, J. & Cobb, M. H. Purification of casein kinase I and isolation of cDNAs encoding multiple casein kinase I-like enzymes. *Proc Natl Acad Sci USA* 88, 9548-52 (1991).
21. Brockman, J. L., Gross, S. D., Sussman, M. R. & Anderson, R. A. Cell cycle-dependent localization of casein kinase I to mitotic spindles. *Proc Natl Acad Sci USA* 89, 9454-8 (1992).
22. Hoekstra, M. F. et al. HRR25, a putative protein kinase from budding yeast: association with repair of damaged DNA. *Science* 253, 1031-4 (1991).
23. Gross, S. D., Simerly, C., Schatten, G. & Anderson, R. A. A casein kinase I isoform is required for proper cell cycle progression in the fertilized mouse oocyte. *J Cell Sci* 110 (Pt 24), 3083-90 (1997).
24. Gross, S. D., Loijens, J. C. & Anderson, R. A. The casein kinase Ialpha isoform is both physically positioned and functionally competent to regulate multiple events of mRNA metabolism. *J Cell Sci* 112 (Pt 16), 2647-56 (1999).
25. Gross, S. D., Hoffman, D. P., Fisette, P. L., Baas, P. & Anderson, R. A. A phosphatidylinositol 4,5-bisphosphate-sensitive casein kinase I alpha associates with synaptic vesicles and phosphorylates a subset of vesicle proteins. *J Cell Biol* 130, 711-24 (1995).
26. Sauer, B. & Henderson, N. Site-specific DNA recombination in mammalian cells by the Cre recombinase of bacteriophage P1. *Proc Natl Acad Sci USA* 85, 5166-70 (1988).
27. Sternberg, N. & Hamilton, D. Bacteriophage P1 site-specific recombination. I. Recombination between loxP sites. *J Mol Biol* 150, 467-86 (1981).
28. Morin, P. J. et al. Activation of beta-catenin-Tcf signaling in colon cancer by mutations in beta-catenin or APC. *Science* 275, 1787-90 (1997).
29. Vogelstein, B. & Kinzler, K. W. Cancer genes and the pathways they control. *Nat Med* 10, 789-99 (2004).
30. Larue, L. & Delmas, V. The WNT/Beta-catenin pathway in melanoma. *Front Biosci* 11, 733-42 (2006).
31. Legoix, P. et al. Beta-catenin mutations in hepatocellular carcinoma correlate with a low rate of loss of heterozygosity. *Oncogene* 18, 4044-6 (1999).
32. Liu, W. et al. Mutations in AXIN2 cause colorectal cancer with defective mismatch repair by activating beta-catenin/TCF signalling. *Nat Genet* 26, 146-7 (2000).
33. Satoh, S. et al. AXIN1 mutations in hepatocellular carcinomas, and growth suppression in cancer cells by virus-mediated transfer of AXIN1. *Nat Genet* 24, 245-50 (2000).
34. Laurent-Puig, P., Beroud, C. & Soussi, T. APC gene: database of germline and somatic mutations in human tumors and cell lines. *Nucleic Acids Res* 26, 269-70 (1998).
35. Fodde, R., Smits, R. & Clevers, H. APC, signal transduction and genetic instability in colorectal cancer. *Nat Rev Cancer* 1, 55-67 (2001).
36. Korinek, V. et al. Constitutive transcriptional activation by a beta-catenin-Tcf complex in APC-/- colon carcinoma. *Science* 275, 1784-7 (1997).
37. Smits, R. et al. Apc1638T: a mouse model delineating critical domains of the adenomatous polyposis coli protein involved in tumorigenesis and development. *Genes Dev* 13, 1309-21 (1999).
38. Polakis, P. Mutations in the APC gene and their implications for protein structure and function. *Curr Opin Genet Dev* 5, 66-71 (1995).
39. Shih, I. M., Yu, J., He, T. C., Vogelstein, B. & Kinzler, K. W. The beta-catenin binding domain of adenomatous polyposis coli is sufficient for tumor suppression. *Cancer Res* 60, 1671-6 (2000).
40. Cliffe, A., Mieszczanek, J. & Bienz, M. Intracellular shuttling of a *Drosophila* APC tumour suppressor homolog. *BMC Cell Biol* 5, 37 (2004).
41. Fabbro, M. & Henderson, B. R. Regulation of tumor suppressors by nuclear-cytoplasmic shuttling. *Exp Cell Res* 282, 59-69 (2003).
42. Henderson, B. R. Nuclear-cytoplasmic shuttling of APC regulates beta-catenin subcellular localization and turnover. *Nat Cell Biol* 2, 653-60 (2000).
43. Henderson, B. R. & Fagotto, F. The ins and outs of APC and beta-catenin nuclear transport. *EMBO Rep* 3, 834-9 (2002).
44. Neufeld, K. L. et al. Adenomatous polyposis coli protein contains two nuclear export signals and shuttles between the nucleus and cytoplasm. *Proc Natl Acad Sci USA* 97, 12085-90 (2000).
45. Rosin-Arbesfeld, R., Cliffe, A., Brabletz, T. & Bienz, M. Nuclear export of the APC tumour suppressor controls beta-catenin function in transcription. *Embo J* 22, 1101-13 (2003).
46. Rosin-Arbesfeld, R., Townsley, F. & Bienz, M. The APC tumour suppressor has a nuclear export function. *Nature* 406, 1009-12 (2000).
47. Hamada, F. & Bienz, M. The APC tumor suppressor binds to C-terminal binding protein to divert nuclear beta-catenin from TCF. *Dev Cell* 7, 677-85 (2004).
48. Sierra, J., Yoshida, T., Joazeiro, C. A. & Jones, K. A. The APC tumor suppressor counteracts beta-catenin activation and H3K4 methylation at Wnt target genes. *Genes Dev* 20, 586-600 (2006).
49. Powell, S. M. et al. APC mutations occur early during colorectal tumorigenesis. *Nature* 359, 235-7 (1992).
50. Green, R. A., Wollman, R. & Kaplan, K. B. APC and EB1 function together in mitosis to regulate spindle dynamics and chromosome alignment. *Mol Biol Cell* 16, 4609-22 (2005).
51. Kaplan, K. B. et al. A role for the Adenomatous Polyposis Coli protein in chromosome segregation. *Nat Cell Biol* 3, 429-32 (2001).
52. Fodde, R. et al. Mutations in the APC tumour suppressor gene cause chromosomal instability. *Nat Cell Biol* 3, 433-8 (2001).
53. Chen, L., Li, C., Pan, Y. & Chen, J. Regulation of p53-MDMX interaction by casein kinase 1 alpha. *Mol Cell Biol* 25, 6509-20 (2005).

54. Kawai, H. et al. DNA damage-induced MDMX degradation is mediated by MDM2. *J Biol Chem* 278, 45946-53 (2003).
55. Benosman, S. et al. Multiple neurotoxic stresses converge on MDMX proteolysis to cause neuronal apoptosis. *Cell Death Differ* 14, 2047-57 (2007).
56. Pereg, Y. et al. Phosphorylation of Hdmx mediates its Hdm2- and ATM-dependent degradation in response to DNA damage. *Proc Natl Acad Sci USA* 102, 5056-61 (2005).
57. Donehower, L. A. et al. Mice deficient for p53 are developmentally normal but susceptible to spontaneous tumours. *Nature* 356, 215-21 (1992).
58. Macleod, K. F. et al. p53-dependent and independent expression of p21 during cell growth, differentiation, and DNA damage. *Genes Dev* 9, 935-44 (1995).
59. Holmberg, C., Helin, K., Sehested, M. & Karlstrom, O. E2F-1-induced p53-independent apoptosis in transgenic mice. *Oncogene* 17, 143-55 (1998).
60. Irwin, M. et al. Role for the p53 homologue p73 in E2F-1-induced apoptosis. *Nature* 407, 645-8 (2000).
61. Field, S. J. et al. E2F-1 functions in mice to promote apoptosis and suppress proliferation. *Cell* 85, 549-61 (1996).
62. Ginsberg, D. E2F1 pathways to apoptosis. *FEBS Lett* 529, 122-5 (2002).
63. Moon, N. S. et al. *Drosophila* E2F1 has context-specific pro- and antiapoptotic properties during development. *Dev Cell* 9, 463-75 (2005).
64. Ambrosini, G. et al. Mouse double minute antagonist Nutlin-3a enhances chemotherapy-induced apoptosis in cancer cells with mutant p53 by activating E2F1. *Oncogene* 26, 3473-81 (2007).
65. Stanelle, J. & Putzer, B. M. E2F1-induced apoptosis: turning killers into therapeutics. *Trends Mol Med* 12, 177-85 (2006).
66. Petrocca, F. et al. E2F1-regulated microRNAs impair TGFbeta-dependent cell-cycle arrest and apoptosis in gastric cancer. *Cancer Cell* 13, 272-86 (2008).
67. Greten, F. R. et al. IKKbeta links inflammation and tumorigenesis in a mouse model of colitis-associated cancer. *Cell* 118, 285-96 (2004).
68. Lee, J. et al. Maintenance of colonic homeostasis by distinctive apical TLR9 signalling in intestinal epithelial cells. *Nat Cell Biol* 8, 1327-36 (2006).

What is claimed is:

1. A method of preventing colorectal cancer in a subject having a mutation in an Adenomatous polyposis coli (APC) gene, the method comprising administering to the subject a therapeutically effective amount of an inhibitor of Casein kinase I (CKI), said CKI being selected from the group consisting of CKIα and CKIδ, thereby preventing the colorectal cancer.

2. The method of claim 1, wherein said inhibitor of CKI is selected from the group consisting of small chemical inhibitor and a polynucleotide inhibitor.

3. The method of claim 2, wherein said polynucleotide inhibitor comprises an RNA silencing agent.

4. The method of claim 1, wherein when said inhibitor is of CK1delta the method further comprises inhibiting CK1epsilon.

5. A method of treating or preventing colorectal cancer in a subject having a mutation in an APC gene, the method comprising administering to the subject a therapeutically effective amount of an inhibitor of CKI, said CKI being selected from the group consisting of CKIα and CKIδ, thereby treating or preventing the cancer.

6. The method of claim 5, wherein said inhibitor of CKI is selected from the group consisting of small chemical inhibitor and a polynucleotide inhibitor.

7. The method of claim 6, wherein said polynucleotide inhibitor comprises an RNA silencing agent.

8. A method of treating or preventing colorectal cancer in a subject having a mutation in an Adenomatous polyposis coli (APC) gene, the method comprising administering to the subject a therapeutically effective amount of an inhibitor of Casein kinase I delta (CKIδ) thereby treating or preventing the colorectal cancer.

9. The method of claim 8, wherein said inhibitor of CKIδ is selected from the group consisting of small chemical inhibitor and a polynucleotide inhibitor.

10. The method of claim 9, wherein said polynucleotide inhibitor comprises an RNA silencing agent.

11. The method of claim 8, further comprising administering to the subject a therapeutically effective amount of an inhibitor of Casein kinase I alpha (CKIα).

* * * * *